United States Patent [19]

Maraganore et al.

[11] Patent Number: 5,242,810

[45] Date of Patent: Sep. 7, 1993

[54] BIFUNCTIONAL INHIBITORS OF THROMBIN AND PLATELET ACTIVATION

[75] Inventors: John M. Maraganore, Tewksbury; Betty H. Chao, Winchester; Kathryn L. Strauch, Newton; Jeffrey S. Thompson, Woburn, all of Mass.

[73] Assignee: Biogen, Inc., Cambridge, Mass.

[21] Appl. No.: 623,611

[22] Filed: Dec. 7, 1990

[51] Int. Cl.$^5$ .................. C12P 21/06; C12N 9/74; C12N 15/00; A61K 37/64

[52] U.S. Cl. .................. 435/69.2; 435/69.6; 435/69.7; 435/214; 435/252.3; 435/252.33; 435/172.3; 435/320.1; 530/324; 530/856; 930/250; 536/23.4; 536/23.5; 536/23.1

[58] Field of Search .............. 435/214, 69.2, 69.6, 435/69.7, 252.3, 172.3, 252.33, 320.1; 930/250; 530/324, 856; 536/27; 935/47, 10

[56] References Cited

U.S. PATENT DOCUMENTS

| | | | |
|---|---|---|---|
| 3,743,722 | 7/1973 | Nolan | 424/98 |
| 3,879,369 | 4/1975 | Nolan | 260/112 |
| 4,341,762 | 7/1982 | Haast | 424/88 |
| 4,578,079 | 3/1986 | Ruoslahti et al. | 623/11 |
| 4,610,879 | 9/1986 | Markland et al. | 424/94 |
| 4,683,291 | 7/1987 | Zimmerman et al. | 530/324 |
| 4,741,902 | 5/1988 | Haast | 424/88 |
| 4,792,525 | 12/1988 | Ruoslahti et al. | 435/240.243 |
| 4,971,953 | 11/1990 | Krstenansky | 514/14 |

FOREIGN PATENT DOCUMENTS

| | | |
|---|---|---|
| 276014 | 7/1988 | European Pat. Off. |
| 291981 | 11/1988 | European Pat. Off. |
| 291982 | 11/1988 | European Pat. Off. |
| 317053 | 5/1989 | European Pat. Off. |
| 333356 | 9/1989 | European Pat. Off. |
| 338634 | 10/1989 | European Pat. Off. |
| 341607 | 11/1989 | European Pat. Off. |
| 0382451 | 8/1990 | European Pat. Off. |
| WO90/03391 | 4/1990 | PCT Int'l Appl. |
| WO90/06128 | 6/1990 | PCT Int'l Appl. |
| WO90/06134 | 6/1990 | PCT Int'l Appl. |
| WO90/11783 | 10/1990 | PCT Int'l Appl. |
| WO91/02750 | 3/1991 | PCT Int'l Appl. |
| WO91/19734 | 12/1991 | PCT Int'l Appl. |
| 9008772 | 8/1990 | World Int. Prop. O. |

OTHER PUBLICATIONS

Suggs et al., *PNAS*, vol. 78, No. 11, Nov. 1981, pp. 6613-6617.
Chao et al., *PNAS*, vol. 86, Oct. 1989, pp. 8050-8054.
Guan et al., *Gene*, vol. 67, 1988, pp. 21-30.
Ghrayeb et al., *EMBO Journal*, vol. 3, No. 10, 1984, pp. 2437-2442.
N. Ahmed et al., "Characterization of a Fibrinolytic Enzyme from the Venom of Agkistrodon Contortrix", *FASEB J.*, 4, p. A1232, Abstract 5611 (Feb. 28, 1990).
S. Bajusz et al., "Inhibition of Thrombin and Trypsin by Tripeptide Aldehydes", *Int. J. Peptide Protein Res.*, 12, pp. 217-221 (Oct. 1978).

(List continued on next page.)

*Primary Examiner*—Robert A. Wax
*Assistant Examiner*—Keith D. Hendricks
*Attorney, Agent, or Firm*—Margaret A. Pierri; Andrew S. Marks; Loretta A. Miraglia

[57] ABSTRACT

The present invention relates to novel, bifunctional inhibitors of both platelet activation and thrombin. These bifunctional inhibitors are characterized by two domains — a glycoprotein IIb/IIIa inhibitory domain and a thrombin inhibitory domain. The invention also relates to DNA sequences which encode the bifunctional inhibitors of this invention, recombinant DNA molecules which contain these DNA sequences and host transformed with these DNA molecules. The invention further relates to he recombinant expression of the bifunctional inhibitors of this invention by transformed hosts as well as to methods for purifying such recombinant bifunctional inhibitors. This invention also provides compositions and methods employing the novel bifunctional inhibitors alone or together with a fibrinolytic agent. Such compositions may be useful in patients for treating thrombotic disease, increasing reocclusion time, decreasing reperfusion time, simultaneously inhibiting thrombin- and platelet-mediated functions and inhibiting malignant cell growth.

12 Claims, 15 Drawing Sheets

S. S. Bajwa et al., "Thrombin-Like and Fibrinolytic Enzymes in the Venoms from the Gaboon Viper (*Bitis gabonica*), Eastern Cottonmouth Moccasin (*Agkistrodon p. piscivorus*) and Southern Copperhead (*Agkistrodon c. contortrix*) Snakes", *Toxicon*, 20, pp. 427–432 (Apr. 21, 1982).

C. Bergmann et al., "Chemical Synthesis and Expression of a Gene Coding for Hirudin, the Thrombin-Specific Inhibitor from the Leech *Hirudo medicinalis*", *Biol. Chem. Hoppe-Seyler*, 367, pp. 731–740 (Aug. 24–29, 1986).

W. Bode et al., "The Refined 1.9 Å Crystal Structure of Human α-Thrombin: Interaction with D-Phe-Pro-Arg Chloromethylketone and Significance of the Tyr-Pro-Pro-Trp Insertion Sequence", *EMBO J.*, 8, pp. 3467–3475 (Nov. 1989).

J.-Y. Chang, "The Functional Domain of Hirudin, a Thrombin-Specific Inhibitor", *FEBS Lett.*, 164, pp. 307–313 (Dec. 1983).

B. Chao et al., "Applaggin: A Potent Inhibitor of Platelet Aggregation and Secretion", *Thrombosis & Haemostasis*, 62, p. 50, Abstract No. 120 (Aug. 19, 1989).

M. S. Dennis et al., "Platelet Glycoprotein IIb-IIIa Protein Antagonists from Snake Venoms: Evidence for a Family of Platelet-Aggregation Inhibitors", *Proc. Natl. Acad. Sci. USA*, 87, pp. 2471–2475 (Apr. 1990).

A. Falanga et al., "Isolation and Characterization of Cancer Procoagulant: A Cysteine Proteinase from Malignant Tissue", *Biochemistry*, 24, pp. 5558–5567 (Sep. 24, 1985).

A. Falanga et al., "A New Procoagulant in Acute Leukemia", *Blood*, 71, pp. 870–875 (Apr. 1988).

J. W. Fenton II, "Regulation of Thrombin Generation and Function", *Semin. Thromb. Hemost.*, 14, pp. 234–240 (Jul. 1988).

J. W. Fenton II, "Thrombin Bioregulatory Functions", *Adv. Clin. Enzymol.*, 6, pp. 186–193 (1988).

J. W. Fenton II et al., "Thrombin Anion-binding Exosite Interactions with Heparin and Various Polyanions", *Ann. New York Acad. Sci.*, 556, pp. 158–165 (Jun. 7, 1989).

E. Fortkamp et al., "Cloning and Expression in *Escherichia coli* of a Synthetic DNA for Hirudin, the Blood Coagulation Inhibitor in the Leech", *DNA*, 5, pp. 511–517 (Dec. 1986).

B. Furie et al., "Computer-generated Models of Blood Coagulation Factor Xa, Factor IXa, and Thrombin Based upon Structural Homology with Other Serine Proteases", *J. Biol. Chem.*, 257, pp. 3875–3882 (Apr. 10, 1982).

Z.-R. Gan et al., "Echistatin: A Potent Platelet Aggregation Inhibitor from the Venom of the Viper, *Echis carinatus*", *J. Biol. Chem.*, 263, pp. 19827–19832 (Dec. 25, 1988).

S. G. Gordon et al., "Cysteine Proteinase Procoagulant From Amnion-Chorion", *Blood*, 66, pp. 1261–1265 (Dec. 1985).

D. Gurwitz et al., "Thrombin Modulates and Reverses Neuroblastoma Neurite Outgrowth", *Proc. Natl. Acad. Sci. USA*, 85, pp. 3440–3444 (May 1988).

S. R. Hanson et al., "Interruption of Acute Platelet-dependent Thrombosis by the Synthetic Antithrombin D-phenylalanyl-L-prolyl-L-arginyl Chloromethyl Ketone", *Proc. Natl. Acad. Sci. USA*, 85, pp. 3184–3188 (May 1988).

R. P. Harvey et al., "Cloning and Expression of a cDNA Coding for the Anticoagulant Hirudin from the Bloodsucking Leech, *Hirudo medicinalis*", *Proc. Natl. Acad. Sci. USA*, 83, pp. 1084–1088 (Feb. 1986).

T.-F. Huang et al., "Characterization of Hemorrhagic Principles from *Trimeresurus gramineus* Snake Venom", *Toxicon*, 22, pp. 45–52 (Mar. 22, 1984).

T.-F. Huang et al., "Characterization of a Potent Platelet Aggregation Inhibitor from *Agkistrodon rhodostoma* Snake Venom", *Biochim. et Biophys. Acta*, 925, pp. 248–257 (Sep. 11, 1987).

T.-F. Huang et al., "Trigramin: A Low Molecular Weight Peptide Inhibiting Fibrinogen Interaction with Platelet Receptors Expressed on Glycoprotein IIb-IIIa Complex", *J. Biol. Chem.*, 262, pp. 16157–16163 (Nov. 25, 1987).

T.-F. Huang et al., "Trigramin: Primary Structure and Its Inhibition of von Willebrand Factor Binding to Glycoprotein IIb/IIIa Complex on Human Platelets", *Biochemistry*, 28, pp. 661–666 (Jan. 24, 1989).

M. J. Humphries et al., "Investigation of the Biological Effects of Anti-Cell Adhesive Synthetic Peptides that Inhibit Experimental Metastasis of B16-F10 Murine Melanoma Cells", *J. Clin. Invest.*, 81, pp. 782–790 (Mar. 1988).

J. A. Jakubowski et al., "Inhibition of Coagulation and Thrombin-Induced Platelet Activities by a Synthetic Dodecapeptide Modeled on the Carboxy-Terminus of Hirudin", *Blood*, 75, pp. 399–406 (Jan. 1990).

A. Kelly et al., "Potent Antithrombotic Effects of a Novel Hybrid Antithrombin Peptide In Vivo", *Circulation*, 82, pp. III-603, Abstract 2397 (Oct. 1990).

C. Kettner et al., "D-Phe-Pro-ArgCh$_2$Cl-A Selective Affinity Label for Thrombin", *Thrombosis Res.*, 14, pp. 969–973 (1979).

P. Klement et al., "Effects of Heparin and Hirulog on tPA-Induced Thrombolysis in a Rat Model", *Fibrinolysis*, 4, p. 9, Abstract 27 (Aug. 4–8, 1990).

K. A. Knudsen et al., "Trigramin, An RGD-Containing Peptide from Snake Venom, Inhibits Cell-Substratum Adhesion of Human Melanoma Cells", *Exper. Cell Res.*, 179, pp. 42–49 (Nov. 1988).

S. Konno et al., "Analysis of the Secondary Structure of Hirudin and the Mechanism of Its Interaction with Thrombin", *Arch. Biochem. Biophys.*, 267, pp. 158–166 (Nov. 15, 1988).

J. L. Krstenansky et al., "Anticoagulant Peptides: Nature of the Interaction of the C-Terminal Region of Hirudin with a Noncatalytic Binding Site on Thrombin", *J. Med. Chem.*, 30, pp. 1688–1691 (Sep. 1987).

J. L. Krstenansky et al., "Antithrombin Properties of C-Terminus of Hirudin Using Synthetic Unsulfated N$^\alpha$-acetyl-hirudin$_{45-65}$", *FEBS Lett.*, 211, pp. 10–16 (Jan. 1987).

J. L. Krstenansky et al., "Hirudin and Hirullin C-Terminal Domains: Structural Comparisons and Antithrombin Properties", *Circulation*, 82, p. II-659, Abstract 2619 (Oct. 1990).

J. L. Krstenansky et al., "Development of MDL 28,050, a Small Stable Antithrombin Agent Based on a Functional Domain of the Leech Protein, Hirudin", *Thrombosis & Haemostasis*, 63, pp. 208–214 (Apr. 12, 1990).

J. M. Maraganore et al., "Anticoagulant Activity of Synthetic Hirudin Peptides", *J. Biol. Chem.*, 264, pp. 8692–8698 (May 25, 1989).

J. M. Maraganore et al., "Design and Characterization of Hirulogs: A Novel Class of Bivalent Peptide Inhibitors of Thrombin", *Biochemistry*, 29, 7095–7101 (Jul. 31, 1990).

C. Ouyang et al., "Potent Platelet Aggregation Inhibitor from *Trimeresurus gramineus* Snake Venom", *Biochim. et Biophys. Acta*, 757, pp. 332–341 (Jun. 9, 1983).

C. Ouyang et al., "α-Fibrinogenase from *Agkistrodon rhodostoma* (Malayan Pit Viper) Snake Venom", *Toxicon*, 21, pp. 25–33 (Mar. 18, 1983).

C. Ouyang et al., "A Potent Platelet Aggregation Inhibitor Purified from *Agkistrodon halys* (Mamushi) Snake Venom", *Toxicon*, 21, pp. 797–804 (Dec. 21, 1983).

C. Ouyang et al., "Characterization of the Platelet Aggregation Inducer and Inhibitor from *Echis carinatus* Snake Venom", *Biochim. et Biophys. Acta*, 841, pp. 1–7 (Jul. 26, 1985).

T. J. Owen et al., "N-Terminal Requirements of Small Peptide Anticoagulants Based on Hirudin$_{54-65}$", *J. Med. Chem.*, 31, pp. 1009–1111 (May 9, 1988).

T. J. Rydel et al., "The Structure of a Complex of Recombinant Hirudin and Human α-Thrombin", *Science*, 249, pp. 277–280 (Jul. 20, 1990).

B. Savage, "Binding of the Snake Venom-Derived Proteins Applaggin and Echistatin to the Arginine--Glycine-Aspartic Aci Recognition Site(s) on Platelet Glycoprotein IIb-IIIa Complex Inhibits Receptor Function," *J. Biol. Chem.*, 265, pp. 11766–11767 (Jul. 15, 1990).

S. R. Stone et al., "Kinetics of the Inhibition of Thrombin Hirudin", *Biochemistry*, 25, pp. 4622–4628 (Aug. 12, 1986).

C.-M. Teng et al., "Properties of a Potent Platelet Aggregation Inhibitor from *Echis carinatus* Snake Venom", in *Hemostasis and Animal Venoms*, H. Pirkle et al., eds., Marcel Dekker, Inc., New York, pp. 399–409 (Mar. 14, 1988).

```
DNS                    B   A   BM              B         X       E
sct                    s   p   sg  D           s         h       a
aoy                    m   a   pi  r           p         o       e
111                    1   L   1A  a           M         2       1
                           1   21  3           1
    /                  /   /       /           /         /       /
1   CATGGAAGCTGGTGAAGAATGCGACTGCGACTGCGGATCCCCGGAAAACCCGTGCTGCGACGCGG
    ----+----+----+----+----+----+----+----+----+----+----+----+ 60
    GGTACCTTCGACCACTTCTTACGCTGACGCTGACGCCTAGGGGCCTTTTGGGCACGACGCTGCGCC
    MetGluAlaGlyGluCysAspCysAspCysGlySerProGluAsnProCysCysAspAlaAla 61  CCACCTGCAAACTTCGTCCGGGTGCACAGTGTGCAGAAGGTCTGTGCTGCGACCAGTGCA
    ----+----+----+----+----+----+----+----+----+----+----+----+ 120
    GGTGGACGTTTGAAGCAGGCCCACGTGTCACACGTCTTCCAGACACGACGCTGGTCACGT
    ThrCysLysLeuArgProGlyAlaGlnCysAlaGluGlyLeuCysCysAspGlnCysLys
```

FIG. 1

```
       B        A         K
       s       sB         p
       p       pa         n
       E       7n         1
       1       11
          \        \  /
     AATTCATGAAAGAAGGTACCGTTTGCCGTCGTGCTCGAGGTGACGACGTTAACGACTACT
121  ---------+---------+---------+---------+---------+---------+  180
     TTAAGTACTTTCTTCCATGGCAAACGGCAGCACGAGCTCCACTGCTGCAATTGCTGATGA
     PheMetLysGluGlyThrValCysArgArgAlaArgGlyAspAspValAsnAspTyrCys

BH                              H
                                AsgX                            iH
                                vpih                            np
                                alAo                            ca
                                1211                            21
                                 \ //                            /
     GCAACGGTATCTCTGCAGGTTGCCCGCGTAACCCGTTCCACTGATGA
181  ---------+---------+---------+---------+------+  232
     CGTTGCCATAGAGACGTCCAACGGGCATTGGGCAAGGTGACTACTTCGA
     AsnGlyIleSerAlaGlyCysProArgAsnProPheHisEndEndSer???
```

| | |
|---|---|
| 1 | CATGGAAGCTGGTGAAGAATGCG |
| 2 | CTTCGACCACTTCTTACGCTGACGCCTAGGG |
| 3 | GATCCCCGGAAAACCCGTGCTGCGACGC |
| 4 | GCCTTTTGGGCACGACGCTGCGCCGGTG |
| 5 | GGCCACCTGCAAACTTCGTCCGGGTGCACAGTGT |
| 6 | GACGTTTGAAGCAGGCCCACGT |
| 7 | GCAGAAGGTCTGTGCTGCGACCAGTGCAAAT |
| 8 | GTCACACGTCTTCCAGACACGACGCTGGTCACGTTTAAGTACT |
| 9 | TCATGAAAGAAGGTACCGTTTGCCGTCGTGC |
| 10 | TTCTTCCATGGCAAACGGCAGCACGAGCTCC |
| 11 | TCGAGGTGACGACGTTAACGACTACTGCAACGG |
| 12 | ACTGCTGCAATTGCTGATGACGAAGCCATAGAG |
| 13 | TATCTCTGCAGGTTGCCCGCGTAACCCGTTCCACTGATGA |
| 14 | ACGTCCAACGGGCGCATTGGGCAAGGTGACTACTTCGA |

FIG. 2

```
                                    H                E
 N    N     S                       i        K S     c      B
 h    o     a                       n        p m     o      g
 e    t     c                       d        n a     R      l
 1    1     2                       3        1 1     1      2
GCTAGCGGCCGCGGTCCAACCACCAATCTCAAAGCTTGGTACCCGGGAATTCAGATCTGC
----------+----------+----------+----------+----------+----------+
CGATCGCCGGCGCCAGGTTGGTGGTTAGAGTTTCGAACCATGGGCCCTTAAGTCTAGACG

E          B
 P    SX    SX       c C    N   a                        NS
 s    ph    ab       o l    c   m                        oa
 t    ho    ca       R a    o   H                        tc
 1    11    11       5 1    1   1                        12
                /                                       /
AGCATGCTCGAGCTCTAGATATCGATTCCATGGATCCTCACATCCCAATCCGCGGCCGCA
----------+----------+----------+----------+----------+----------+
TCGTACGAGCTCGAGATCTATAGCTAAGGTACCTAGGAGTGTAGGGTTAGGCGCCGGCGT
```

FIG. 3

```
1    CATGGGTCCGCGTCCGGGTGGTGGTGGTAACGGTGAC
2         CCAGGCGCAGGCCCACCACCACCATTGCCACTGAAGC

3    TTCGAAGAAATCCCGGAAGAATACCTGG
4         TTCTTTAGGGCCTTCTTATGGACCCACC

5    GTGGTGGTGGTGAAGCTGGTGAAGAATGCG
6         ACCACCACTTCGACCACTTCTTAC
```

FIG. 5

```
1         GGTTGCCCGCGTAACCCGTTCCACGGTG
2    ACGTCCAACGGGCGCATTGGGCAAGGTG

3         GTGGTGGTGGTCCGCGTCCGGGTGGTGGTGGTAACGGTGAC
4    CCACCACCACCACCAGGCGCAGGCCCACCACCACCATTGCCACTGAAGC

5    TTCGAAGAAATCCCGGAAGAATACCTGTGATGA
6         TTCTTTAGGGCCTTCTTATGGACACTACTTCGA
```

FIG. 6 malE ... TCG AGC TCG GTA CCC GGC CGG GGA TCC ATC GAG GGT AGG CCT GAA TTC ATG appilog
        Ser Ser Ser Val Pro Gly Arg Gly Ser Ile Glu Gly Arg Pro Glu Phe Met
                                        ↑
                                  FACTOR Xa
                                  CLEAVAGE SITE

FIG. 10

BIFUNCTIONAL INHIBITORS OF THROMBIN AND PLATELET ACTIVATION

TECHNICAL FIELD OF THE INVENTION

The present invention relates to novel, bifunctional inhibitors of both platelet activation and thrombin. These bifunctional inhibitors are characterized by two domains — a glycoprotein IIb/IIIa inhibitory domain and a thrombin inhibitory domain. The invention also relates to DNA sequences which encode the bifunctional inhibitors of this invention, recombinant DNA molecules which contain these DNA sequences and hosts transformed with these DNA molecules. The invention further relates to the recombinant expression of the bifunctional inhibitors of this invention by transformed hosts as well as to methods for purifying such recombinant bifunctional inhibitors. This invention also provides compositions and methods employing the novel bifunctional inhibitors alone or together with a fibrinolytic agent. Such compositions may be useful in patients for treating thrombotic disease, increasing reocclusion time, decreasing reperfusion time, simultaneously inhibiting thrombin- and platelet-mediated functions and inhibiting malignant cell growth.

BACKGROUND ART

Both platelet activation and thrombin-mediated clot formation are essential to hemostasis. However, perturbations in either of these two hemostatic mechanisms may result in the formation of pathogenic thrombi (blood clots) which block blood flow to dependent tissues. This is the case in a variety of life-threatening vascular diseases, such as myocardial infarction, stroke, peripheral arterial occlusion and other blood system thromboses. Since various biochemical pathways contribute to vascular disease, treatment and prevention may focus on either inhibiting platelets, inhibiting thrombin or directly dissolving the blood clot.

Therefore, strategies to control platelet aggregation and release are desirable in the treatment of vascular disease [L. A. Harker and M. Gent, "The Use of Agents that Modify Platelet Function in the Management of Thrombotic Disorders" in *Hemostasis and Thrombosis*, R. W. Colman et al., eds., pp. 1438-56, J. B. Lippincott, Co., Philadelphia, Penna. (1987)]. Furthermore, inhibition of platelet aggregation may also be desirable in the case of extracorporeal treatment of blood, such as in dialysis, cardiopulmonary bypass surgery, storage of platelets in platelet concentrates and following vascular surgery.

Inhibition of platelets is particularly complicated because many different mechanisms may cause activation. These mechanisms involve one of several different receptors on the platelet surface. Recent attention in this area has been directed to glycoprotein IIb/IIIa, the platelet fibrinogen receptor. This platelet surface protein self-associates as a two-chain complex in a calcium-dependent manner, upon stimulation of platelets with ADP, epinephrine, thrombin or prostaglandin derivatives and precursors thereof [S. J. Shattil et al., "Changes in the Platelet Membrane Glycoprotein IIb/IIIa Complex During Platelet Activation", *J. Biol. Chem.*, 260, pp. 11107-14 (1985); G. A. Marguerie et al., "Human Platelets Possess an Inducible and Saturable Receptor Specific for Fibrinogen", *J. Biol. Chem.*, 254, pp. 5357-63 (1979)]. This results in platelet aggregation mediated by a cross-linking between fibrinogen and the activated glycoprotein IIb/IIIa complexes of two platelets. Glycoprotein IIb/IIIa specifically binds to the Arg-Gly-Asp sequence present in fibrinogen [M. D. Pierschbacher and E. Ruoslahti, "Cell Attachment Activity of Fibronectin Can Be Duplicated By Small Synthetic Fragments of the Molecule", *Nature*, 309, pp. 30-33 (1984); K. M. Yamada and D. W. Kennedy, "Dualistic Nature of Adhesive Protein Function: Fibronectin and Its Biologically Active Peptide Fragments Can Autoinhibit Fibronectin Function", *J. Cell Biol.*, 99, pp. 29-36 (1984); N. Ginsberg et al., "Inhibition of Fibronectin Binding to Platelets By Proteolytic Fragments and Synthetic Peptides Which Support Fibroblast Adhesion", *J. Biol. Chem.*, 260, pp. 3931-36 (1985); E. F. Plow et al., "The Effect of Arg-Gly-Asp-Containing Peptides on Fibrinogen and Von Willebrand Factor Binding to Platelets", *Proc. Nat. Acad. Sci. USA*, 82, pp. 8057-61 (1985); T. K. Gartner and J. S. Bennett, "The Tetrapeptide Analogue of the Cell Attachment Site of Fibronectin Inhibits Platelet Aggregation and Fibrinogen Binding to Activated Platelets", *J. Biol. Chem.*, 260, pp. 11891-94 (1985); M. Kloczewiak et al., "Localization of a Site Interacting With Human Platelet Receptor on Carboxy-Terminal Segment of Human Fibrinogen Gamma Chain", *Biochim. Biophys. Res. Comm.*, 107, pp. 181-87 (1982)].

Specific inhibitors of glycoprotein IIb/IIIa, such as monoclonal antibodies [J. S. Bennett et al., "Inhibition of Fibrinogen Binding to Stimulated Human Platelets By a Monoclonal Antibody", *Proc. Natl. Acad. Sci. USA*, 80, pp. 2417-21 (1983); R. P. McEver et al., "Identification of Two Structurally and Functionally Distinct Sites on Human Platelet Membrane Glycoprotein IIb/IIIa Using Monoclonal Antibodies", *J. Biol. Chem.*, 258, pp. 5269-75 (1983); B. S. Coller, "A New Murine Monoclonal Antibody Reports An Activation-Dependent Change in the Conformation and/or Microenvironment of the Platelet Glycoprotein IIb/IIIa Complex", *J. Clin. Invest.*, 76, pp. 107-08 (1985)] and small Arg-Gly-Asp-containing peptides [T. K. Gartner and J. S. Bennett, supra], are less toxic, faster acting and have a shorter duration of effect as compared to aspirin, the most commonly used platelet inhibitor. Further, unlike aspirin, these compounds are effective against a number of different platelet aggregation mechanisms. Both Arg-Gly-Asp-containing peptides and antibodies toward glycoprotein IIb/IIIa demonstrate antithrombotic efficacy in in vivo models of thrombosis [Y. Cadroy et al., "Potent Antithrombotic Effects of Arg-Gly-Asp-Val (RGDV) Peptide In Vivo", *Circulat., Part II*, 75, p. II-313 (1988); B. S. Coller et al., "Antithrombotic Effect of a Monoclonal Antibody to the Platelet Glycoprotein IIb/IIIa Receptor in an Experimental Animal Model", *Blood*, 68, pp. 783-86 (1986); S. R. Hanson et al., "Effects of Monoclonal Antibodies Against the Platelet Glycoprotein IIb/IIIa Complex on Thrombosis and Hemostasis in the Baboon", *J. Clin. Invest.*, 81, pp. 149-58 (1988); T. Yasuda et al., "Monoclonal Antibody Against the Platelet Glycoprotein (GP) IIb/IIIa Receptor Prevents Coronary Artery Reocclusion Following Reperfusing With Recombinant Tissue-type Plasminogen Activator in Dogs", *J. Clin. Invest.*, 81, pp. 1284-91 (1988); B. S. Coller et al., "Inhibition of Human Platelet Function In Vivo With A Monoclonal Antibody", *Annals Int. Med.*, 109, pp. 635-38 (1988)].

In order to effectively inhibit platelet aggregation, Arg-Gly-Asp-containing peptides must be administered at concentrations greater than $10^{-5}$M. Such high dosages limit the commercial feasibility of those peptides. Monoclonal antibodies to glycoprotein IIb/IIIa are more potent inhibitors of platelet aggregation, but their synthesis in mouse hybridoma cells poses greater potential immunological complications [S. R. Hanson et al., supra]. In addition, Arg-Gly-Asp peptides and antibodies toward glycoprotein IIb/IIIa fail to block platelet secretion. Therefore, these agents may have a limited effectiveness in vivo due to the proaggregating effects of released platelet elements and their subsequent cascade-like activation of the circulating platelet pool. Finally, monoclonal antibodies toward glycoprotein IIb/IIIa are known to induce thrombocytopenia in both sub-human primates and man [S. R. Hanson et al., supra; H. K. Gold et al., "Pharmacodynamic Study of F(ab')$_2$ Fragments of Murine Monoclonal Antibody 7E3 Directed Against Human Platelet Glycoprotein IIb/IIIa in Patients with Unstable Angina Pectoris", *J. Clin. Invest.*, 86, pp. 651-59 (1990)].

Recent attempts to obtain more effective antiplatelet agents have centered around snake venoms, some of which contain glycoprotein IIb/IIIa inhibitors. These include the proteins carinatin, also known as "echistatin", purified from *Echis carinatus* [C. Ouyang et al., "Characterization of the Platelet Aggregation Inducer and Inhibitor from *Echis carinatus* Snake Venom", *Biochim. Biophys. Acta*, 841, pp. 1-7 (1985); European patent application no. 382,538]; trigramin, purified from *Trimeresurus gramineus* [T. F. Huang et al., "Trigramin", *J. Biol. Chem.*, 262, pp. 16157-63 (1987); European patent application no. 317,053]; a novel homodimeric antiplatelet protein, "applaggin", isolated from the venom of *Agkistrodon p. piscivorus* [PCT application No. WO 90/08772]; and others "European patent application no. 382,451]. These glycoprotein IIb/IIIa inhibitors all belong to a family of related snake venom antiplatelet proteins referred to as "disintegrins". Another polypeptide antiplatelet agent, "decorsin", which is structurally related to the disintegrin family, has recently been isolated from the saliva of the leech *Macrobdella decora* [J. L. Seymour et al., "Decorsin", *J. Biol. Chem.* 265, pp. 10143-47 (1990)]. It is thus reasonable to conclude that many if not all blood feeding organisms contain an antiplatelet protein related to the disintegrin family.

All members of the disintegrin family contain a large number of cysteine residues, several intramolecular disulfide bonds and the sequence Arg-Gly-Asp. The Arg-Gly-Asp sequence in disintegrins is one possible interactive site for IIb/IIIa binding [B. Savage et al., "Binding of the Snake Venom-Derived Proteins Applaggin and Echistatin to the Arginine-Glycine-Aspartic Acid Recognition Site(s) on Platelet Glycoprotein IIbIIIa Complex Inhibits Receptor Function", *J. Biol. Chem.*, 265, pp. 11766-72 (1990); M. S. Dennis et al., "Platelet Glycoprotein IIb-IIIa Protein Antagonist from Snake Venoms: Evidence for a Family of Platelet-Aggregation Inhibitors", *Proc. Natl. Acad. Sci. USA*, 87, pp. 2471-75 (1989)], although synthetic mutants of echistatin lacking the Arg residue still exhibit significant, though diminished, antiplatelet activity. Moreover, a disintegrin from *Sistrurus m. barbouri* contains a Lys-Gly-Asp for Arg-Gly-Asp substitution and still exhibits effective antiplatelet activity [R. M. Scarborough et al., "Characterization of a Potent and GpIIb-IIIa Specific Platelet Aggregation Inhibitor from the Venom of the Southeastern Pygmy Rattlesnake", Abstract, *Circulation*, 82, p. III-370 (1990)]. The disintegrins inhibit platelet aggregation by competitively inhibiting fibrinogen or von Willebrand factor binding to the glycoprotein IIb/IIIa receptor [Savage et al., supra]. Disintegrins have been found to indirectly inhibit platelet secretion and eicosanoid metabolism as a result of preventing close cell contact of platelets [B. H. Chao et al., "*Agkistrodon piscivorus piscivorus* Platelet Aggregation Inhibitor: A Potent Inhibitor of Platelet Activation", *Proc. Natl. Acad. Sci. USA*, 86, pp. 8050-54 (1989)].

Disintegrins have been evaluated as anti-thrombotic agents in models of acute platelet-dependent thrombosis and in models of thrombolysis of experimental thrombi [R. J. Shebuski et al., "Characterization and Platelet Inhibitory Activity of Bitstatin, A Potent Arginine-Glycine-Aspartic Acid-Containing Peptide from the Venom of the Viper *Bitis arietans*", *J. Biol. Chem.*, 264, pp. 21550-56 (1989)]. These agents exhibit potent anti-thrombotic effects. However, as with the monoclonal anti-IIb/IIIa antibodies, administration of disintegrins is associated with a transient platelet thrombocytopenia in sub-human primates [S. R. Hanson et al., *J. Clin. Invest.*, 81, pp. 149-58 (1988)] and thus, potentially in man.

Other approaches to the prevention and treatment of vascular disease is the antagonism of thrombin. Thrombin is both a mediator of clot formation and an agonist for platelet activation. Animal studies have shown that inhibition of thrombin alone is a highly effective mechanism for prevention of platelet thrombus formation [S. R. Hanson et al., "Interruption of Acute Platelet-Dependent Thrombosis by the Synthetic Antithrombin D-phenylalanyl-L-propyl-L-arginyl Chloromethyl Ketone", *Proc. Natl. Acad. Sci. USA*, 85, pp. 3184-88 (1988)]. Heparin, the most widely used thrombin inhibitor in treating vascular disease, does not inhibit thrombin directly. Therefore, it has limited efficacy in inhibiting platelets. This is because heparin activity is neutralized by platelet secretory components, e.g., platelet factor 4 [J. A. Jakubowski and J. M. Maraganore, "Inhibition of Coagulation and Thrombin-Induced Platelet Activities by a Synthetic Dodecapeptide Modeled on the Carboxy-Terminus of Hirudin, *Blood*, 75, pp. 399-406 (1990)].

An alternative to heparin is the direct thrombin inhibitor, hirudin, which binds to thrombin forming a stoichiometric complex [S. R. Stone et al., "Kinetics of the Inhibition of Thrombin by Hirudin", *Biochemistry*, 25, pp. 4622-28 (1986)]. Recently, a novel class of hirudin-based peptides has been designed and characterized [J. M. Maraganore et al., "Design and Characterization of Hirulogs: A Novel Class of Bivalent Peptide Inhibitors of Thrombin", *Biochemistry*, 29, pp. 7095-7101 (1990); copending U.S. patent application No. 549,388]. These peptides, called "Hirulogs", are bivalent inhibitors of thrombin, binding to both the catalytic and anion-binding exosite of the enzyme. Hirulogs have been shown to be effective inhibitors of arterial thrombosis in sub-human primates "A. Kelly et al., "Potent Antithrombotic Effects of a Novel Hybrid Antithrombin Peptide In Vivo", Abstract, *Circulation*, 82, p. III-603 (1990)] and to improve vessel patency in models of tPA-induced fibrinolysis [P. Klement et al., "Effects of Heparin and Hirulog on tPA-Induced Thrombolysis in a Rat Model", Abstract, *Fibrinolysis*, 4, p. 9 (1990)]. While hirulogs show promise for the treatment of arterial, platelet-dependent thrombosis, there will be many clinical circumstances where thrombin inhibition alone is insufficient to prevent thrombosis. This is due to the multiplicity of platelet activation agonists, whose importance as mediators of platelets activation may differ depending on the nature of thrombogenesis.

Despite the developments to date, the need still exists for a better inhibitor of platelet activation and thrombus formation. Such an agent should inhibit platelet activation in response to all physiological agonists without causing transient or long-lasting thrombocytopenia. At the same time, such a molecule should inhibit thrombin-mediated fibrin deposition at the site of a clot, thus preventing a clot from growing.

SUMMARY OF THE INVENTION

The present invention provides novel, bifunctional molecules that are capable of inhibiting both platelet activation and thrombin. These bifunctional inhibitors advantageously inhibit platelet-mediated clot formation and growth while simultaneously preventing clot accretion due to fibrin deposition. As will be appreciated from the disclosure to follow, the bifunctional inhibitors of this invention are effective in inhibiting platelet activation associated with vascular disease without causing thrombocytopenia.

The invention also provides compositions comprising these novel bifunctional inhibitors, optionally together with a fibrinolytic agent. These compositions are safe and effective in treating thrombotic disease, for use following vascular or cardiac surgery and for inhibiting metastatic cell growth.

The invention further provides DNA sequences which encode the bifunctional inhibitors disclosed herein as well as vectors comprising those sequences and hosts transformed therewith. The bifunctional inhibitors of this invention may be produced by recombinant DNA techniques, thus allowing for relatively inexpensive production of commercially feasible quantities. Methods for the recombinant production of the bifunctional inhibitors of this invention are provided.

BRIEF DESCRIPTION OF THE DRAWINGS

FIG. 1 depicts the nucleotide sequence of a synthetic gene which encodes an antiplatelet polypeptide from the snake *Agkistrodon p. piscivorus*.

FIG. 2 depicts the 14 separate oligonucleotides used to construct the synthetic gene which encodes an antiplatelet polypeptide from the snake *Agkistrodon p. piscivorus*.

FIG. 3 depicts the polylinker region of the vector pNN03.

FIG. 5 depicts the individual oligonucleotides used to construct the thrombin inhibitory domain portion of the synthetic gene encoding N-appilog.

FIG. 6 depicts the individual oligonucleotides used to construct the thrombin inhibitory domain portion of the synthetic gene encoding C-appilog.

FIG. 10 depicts the DNA and amino acid sequences at the junction between the malE and appilog portions of the malE-appilog fusion protein.

DETAILED DESCRIPTION OF THE INVENTION

Figure 4:
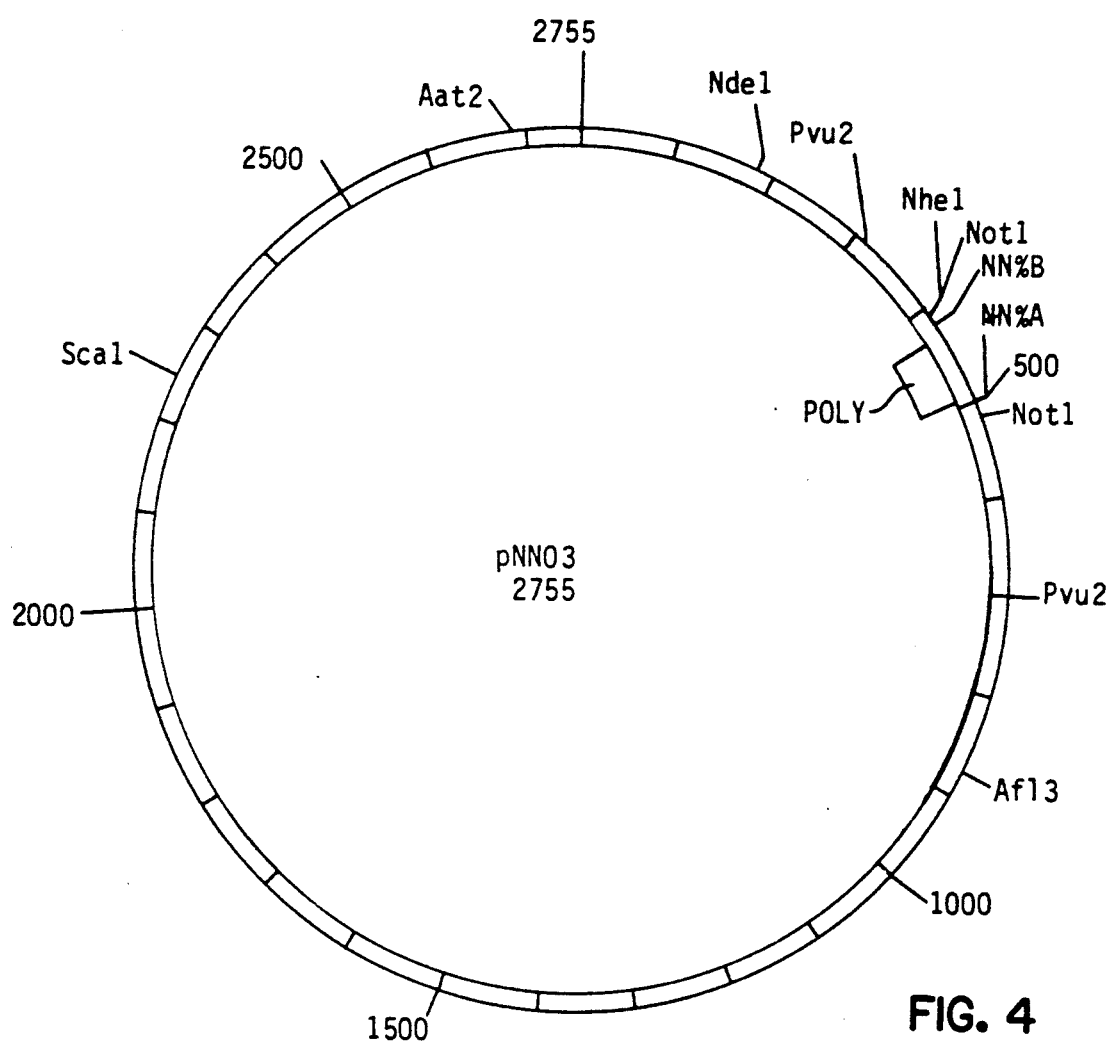
FIG. 4 depicts a restriction map of the vector pNN03.

The following common abbreviations of the amino acids are used throughout the specification and in the claims:

| | |
|---|---|
| His - histidine | Gly - glycine |
| Ala - alanine | Val - valine |
| Leu - leucine | Ile - isoleucine |
| Pro - proline | Phe - phenylalanine |
| Trp - tryptophan | Met - methionine |
| Ser - serine | Thr - threonine |
| Cys - cysteine | Tyr - tyrosine |
| Asn - asparagine | Gln - glutamine |
| Asp - aspartic acid | Glu - glutamic acid |
| Lys - lysine | Arg - arginine |
| BOC - tertButoxycarbonyl | $Tyr(OSO_3^-)$ - tyrosine-O-sulfate |

The term "any amino acid" as used herein includes the L-isomers of the naturally occurring amino acids, as well as other "non-protein" α-amino acids commonly utilized by those in the peptide chemistry arts when preparing synthetic analogs of naturally occurring amino acids. The naturally occurring amino acids are glycine, alanine, valine, leucine, isoleucine, serine, methionine, threonine, phenylalanine, tyrosine, tyrptophan, cysteine, proline, histidine, aspartic acid, asparagine, glutamic acid, glutamine, γ-carboxyglutamic acid, arginine, ornithine and lysine. Examples of "non-protein" α-amino acids include norleucine, norvaline, alloisoleucine, homoarginine, thiaproline, dehydroproline, hydroxyproline, (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or para position of the phenyl moiety with one or two of the following: a ($C_1$– $C_4$) alkyl, a ($C_1$–$C_4$) alkoxy, halogen or nitro groups or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3- and 5-tyrosine sulfonate, 3- and tyrosine carbonate, 3- and 5-tyrosine phosphonate, O-methylsulfate, O-methylphosphate and O-acetate esters of tyrosine, 3,5-diiodotyrosine, 3-and 5-nitrotyrosine, ε-alkyl lysine, delta-alkyl ornithine, and the D-isomers of the naturally occurring amino acids.

The compounds referred to herein as tyrosine sulfate, Tyr(OSO₃⁻) and O-sulfate ester of tyrosine are identical and have the structural formula:

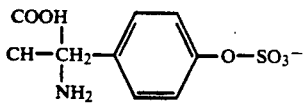

The term "patient" as used in this application refers to any mammal, especially humans.

The term "anionic amino acid" as used herein means a meta, para or ortho, mono- or di-substituted phenylalanine, cyclohexylalanine or tyrosine containing a carboxyl, phosphoryl or sulfonyl moiety, as well as S-alkylated cysteine, S-alkylated homocysteine, γ-carboxyglutamic acid, ε-alkyl lysine, delta-alkyl ornithine, glutamic acid, and aspartic acid. Examples of anionic amino acids are phosphothreonine, phosphoserine, phosphotyrosine, tyrosine sulfate, 3- and 5-tyrosine sulfonate, 3- and 5-tyrosine methyl sulfonate, 3-tyrosine methyl phosphonate and the O-methylsulfate ester of tyrosine.

the term "cationic amino acid" as used herein means arginine, lysine or ornithine.

The terms "catalytic site of thrombin", "active site of thrombin" and "active site pocket of thrombin" as used herein, each refer to any or all of the following sites in thrombin: the substrate binding or "S₁" site; the hydrophobic binding or "oily" site; and the site where cleavage of a substrate is actually carried out ("charge relay site").

The term "backbone chain" as used herein, refers to the portion of a chemical structure that defines the smallest number of consecutive bonds that can be traced from one end of that chemical structure to the other. The atomic components that make up a backbone chain may comprise any atoms that are capable of forming bonds with at least two other atoms.

For example, each of the following chemical structures is characterized by a backbone chain of 7 atoms (the atoms which comprise the backbone chain are indicated in boldface):

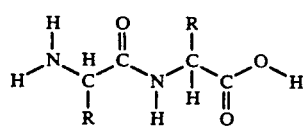

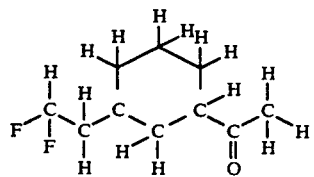

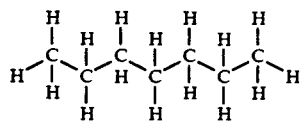

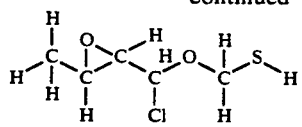

The term "calculated length" as used in this application, refers to a predicted measurement derived by summing up the bond lengths between the atoms which comprise the backbone chain. Bond lengths between any two given atoms are well known in the art [see, for example, *CRC Handbook of Chemistry and Physics, 65th Edition*, R. C. Weist, ed., CRC Press, Inc., Boca Raton, Fla., pp. F-166-70 (1984)].

The present invention relates to novel, bifunctional molecules capable of inhibiting platelet activation and thrombin-mediated functions. These bifunctional inhibitors are characterized by a glycoprotein IIb/IIIa inhibitory domain and a thrombin inhibitory domain. The thrombin inhibitory domain consists of three parts, ordered in an N-terminal to C-terminal direction relative to any amino acids present in this domain: i) a catalytic site-directed moiety that binds to and inhibits the active site of thrombin; ii) a linker moiety characterized by a backbone chain having a calculated length of between about 18Å and about 42Å; and iii) an anion binding exosite associating moiety.

According to the invention, the bifunctional inhibitor may be structured so that the glycoprotein IIb/IIIa inhibitory domain is at the N-terminus and the thrombin inhibitory domain is at the C-terminus or vice versa.

The glycoprotein IIb/IIIa inhibitory domain of the molecule of this invention is defined as the portion capable of inhibiting the interaction between fibrinogen and its receptor, platelet surface glycoprotein IIb/IIIa. Many inhibitors of glycoprotein IIb/IIIa are known in the art and any of these may be employed in the bifunctional inhibitors of this invention. For example, the glycoprotein IIb/IIIa inhibitory domain may be a polyclonal or monoclonal antibody to glycoprotein IIb/IIIa, a small Arg-Gly-Asp containing peptide, an Arg-Tyr-Asp containing peptide, any of the known members of the disintegrin family (i.e., snake venom polypeptides such as trigramin, agkistrostatin, bitstatin, echistatin, applaggin), or a polypeptide which mimics the effect of a disintegrin. Preferably, the glycoprotein IIb/IIIa inhibitory domain is a polypeptide having the amino acid sequence:

$X_1$-Cys-$R_1$-$R_2$-$R_2$-$R_3$-Gly-Asp-$R_4$-$R_2$-$R_2$-$R_2$-$R_2$-Cys-$Y_1$, wherein $X_1$ is hydrogen, at least one amino acid or a bond; $Y_1$ is OH, at least one amino acid or a bond; $R_1$, each $R_2$, either the same or different, and $R_3$ are any amino acid; and $R_4$ is a bond or any amino acid. The above amino acid sequence is present in all disintegrins sequenced to date [European patent application no. 382,451].

More preferably, $R_1$ is a cationic amino acid, $R_3$ is Arg or Lys and $R_4$ is Trp, Phe, Asp or a bond. When $R_3$ is Arg or Lys, the glycoprotein IIb/IIIa inhibitory domain contains an Arg-Gly-Asp or a Lys-Gly-Asp sequence — a sequence present in naturally occurring disintegrins which competitively inhibit the platelet fibrinogen receptor. Most preferably, the glycoprotein IIb/IIIa inhibitory domain of the molecules of this invention comprises the amino acid sequence (SEQ ID NO:1):

```
Glu—Ala—Gly—Glu—Glu—Cys—Asp—Cys—Gly—
Ser—Pro—Glu—Asn—Pro—Cys—Asp—Asp—Ala—
Ala—Thr—Cys—Lys—Leu—Arg—Pro—Gly—Ala—
Gln—Cys—Ala—Glu—Gly—Leu—Cys—Cys—Asp—
Gln—Cys—Lys—Phe—Xaa—Lys—Glu—Gly—Thr—
Val—Cys—Arg—Arg—Ala—Arg—Gly—Asp—Asp—
Val—Asn—Asp—Tyr—Cys—Asn—Gly—Ile—Ser—
Ala—Gly—Cys—Pro—Arg—Asn—Pro—Phe—His.
```

When Xaa is Met, the above sequence is the amino acid sequence of "applaggin" (PCT application No. WO 90/08772, the disclosure of which is herein incorporated by reference), a glycoprotein IIb/IIIa inhibitor from the snake *Agkistrodon p. piscivorus.*

It will be understood that if the inhibitors of this invention are produced by recombinant DNA techniques and the glycoprotein IIb/IIIa inhibitory domain is at the N-terminus of the inhibitor, the above sequence may necessarily comprise additional N-terminal amino acids. For example, if the inhibitor is directly expressed by a recombinant host, this domain will contain an N-terminal methionine, required for initiation of translation. If the inhibitor is expressed as a fusion protein, additional N-terminal amino acids attributed to the host polypeptide portion of the fusion protein and/or linkers used to maintain reading frame between the host polypeptide and the glycoprotein IIb/IIIa inhibitory domain may also be present.

The thrombin inhibitory portion of the molecules of this invention consist of three portions, ordered from N- to C-terminus: a catalytic site-directed moiety ("CSDM"), a linker region, and an anion binding exosite associating moiety ("ABEAM").

According to the present invention, the first moiety, CSDM, binds to the active site of thrombin located at or near about Ser-195 and inhibits or retards the amidolytic or estereolytic activity of thrombin.

According to a preferred embodiment, the CSDM has the formula:

$X_2$-$A_1$-Pro-$A_2$, wherein $X_2$ is hydrogen or from 1 to 12 residues, either the same or different, of any amino acid; $A_1$ is Arg or Lys; and $A_2$ is a bond or from 1 to 3 residues, either the same or different, of any amino acid. The CSDM according to this embodiment binds reversibly to the active site of thrombin. In addition, the bond formed between $A_1$ and Pro is a naturally occurring imide bond, as opposed to an amide bond. The imide bond is cleaved by thrombin at a much slower rate than an amide bond. This accounts for the inhibitory effect of the CSDM.

As stated above, the thrombin inhibitory domain may be located at the N- or C-terminus of the bifunctional inhibitors of this invention. Since the CSDM is always at the N-terminus of the thrombin inhibitory domain, it will either be located at the N-terminus or in the middle of the bifunctional inhibitors of this invention. Most preferably, if the thrombin inhibitory domain is at the N-terminus of the bifunctional inhibitor of this invention, the CSDM consists of the amino acid sequence: Gly-Pro-Arg-Pro (amino acids 11-14 of SEQ ID NO:4), Met-Gly-Pro-Arg-Pro (amino acids 10-14 of SEQ ID NO:4), Ala-Asn-Ser-Gly-Pro-Arg-Pro (amino acids 1-7 of SEQ ID NO:5), Ile-Met-Gly-Pro-Arg-Pro (amino acids 1-6 of SEQ ID NO:6), or Gly-Ser-Ile-Glu-Gly-Arg-Pro-Glu-Phe-Met-Gly-Pro-Arg-Pro (amino acids 1-12 of SEQ ID NO:4. If the thrombin inhibitory domain is at the C-terminus of the bifunctional inhibitors of this invention, the CSDM preferably consists of the amino acid sequence: Gly-Gly-Gly-Gly-Gly-Pro-Arg-Pro (amino acids 83-90 of SEQ ID NO:7)

Other CSDMs which may be employed in the bifunctional inhibitors of the present invention are selected from one of three general groups: those described above which bind reversibly to thrombin and are slowly cleaved; those which bind reversibly to thrombin and cannot be cleaved; and those which bind irreversibly to thrombin. Reversible inhibitors bind to the active site of thrombin through non-covalent interactions, such as ionic bonds, hydrophobic interactions or hydrogen bonding. Irreversible CSDMs form covalent bonds with thrombin.

Examples of non-cleavable, reversible CSDMs are small peptides comprising a derivative of Arg, Lys or ornithine linked by a non-cleavable bond to a backbone chain consisting of from 1 to 9 atoms. The derivative of Arg, Lys or ornithine is characterized by a reduced carboxylate moiety or a carboxylate moiety that is displaced from the α-carbon by a chemical structure characterized by a backbone chain of from 1 to 10 atoms. Examples of such derivatives are β-homoarginine; arginine containing a reduced carboxylate moiety, such as Arg[psi$CH_2$NH]; β-homolysine and β-homoornithine.

Other non-cleavable, reversible CSDMs that may be employed in the bifunctional inhibitors of this invention are benzamidine, DAPA, NAPAP and argatroban (argipidine).

Examples of irreversible CSDMs include, but are not limited to, general serine proteinase inhibitors, such as phenylmethylsulfonylfluoride (PMSF), diisopropylfluoro-phosphate (DFP), tosylprolylchloromethylketone (TPCK) and tosyllysylchloromethylketone (TLCK); heterocyclic protease inhibitors, such as isocoumarins; thrombin-specific inhibitors, such as D-Phe-Pro-Arg-$CHCl_2$ (PPACK); and transition state analogues, such as difluoroketomethylene analogs.

According to the present invention, the second component of the thrombin inhibitory domain of the molecules of this invention is a linker moiety. Because the role of this portion of the bifunctional inhibitor is to provide a bridge between the CSDM and the ABEAM, it is the length of the linker, rather than its structure, that is of prime importance. The calculated length of the backbone chain which characterizes the linker must be at least about 18Å — the distance between the catalytic site and the anion binding exosite of thrombin — and less than about 42Å.

The backbone chain of the linker may comprise any atoms which are capable of bonding to at least two other atoms. Preferably, the backbone chain consists of from 6 to 14 residues, either the same or different, of any amino acid. Most preferably, the linker present in the bifunctional inhibitor of this invention consists of the amino acid sequence: Gly-Gly-Gly-Gly-Asn-Gly-Asp-Phe (amino acids 5-12 of SEQ ID NO:2).

The third portion of the thrombin inhibitory domain of the molecules of this invention is the ABEAM, which binds to the anion binding exosite of thrombin. Preferably, the ABEAM has the formula:

$B_1$-$B_2$-$B_3$-Pro-$B_1$-$B_1$-$B_4$-$Y_2$, wherein each $B_1$, either the same or different, is any anionic amino acid; $B_2$ is any amino acid; $B_3$ is Ile, Val, Leu or Phe; $B_4$ is Tyr, Trp, Phe, Leu, Ile, Val, Pro or a dipeptide consisting of one of these amino acids and any amino acid; and $Y_2$ is OH or from 1 to 5 residues, either the same or different, of any amino acid.

Peptides which are homologous to the carboxy terminal portion of hirudin have been shown to bind to the anion binding exosite on thrombin [copending U.S. patent application no. 314,756 and J. M. Maraganore et al. "Anticoagulant Activity of Synthetic Hirudin Peptides", *J. Biol. Chem.*, 264, pp. 8692-98 (1989); both of which are herein incorporated by reference].

According to a preferred embodiment of this invention, ABEAM is homologous to amino acids 56-64 of hirudin, i.e., each $B_1$ is Glu, $B_2$ is Glu, $B_3$ is Ile and $B_4$ is Tyr-Leu or Tyr(OSO3H)-Leu. In the most preferred embodiment, if the thrombin inhibitory domain is at the N-terminus of the bifunctional inhibitor of this invention, the ABEAM consists of the amino acid sequence: Glu-Glu-Ile-Pro-Glu-Glu-Tyr-Leu-Gly-Gly-Gly-Gly (amino acids 13-24 of SEQ ID NO:2). If the thrombin inhibitory domain is at the C-terminus of the bifunctional inhibitor the ABEAM consists of the amino acid sequence: Glu-Glu-Ile-Pro-Glu-Glu-Tyr-Leu (amino acids 89-96 of SEQ ID NO:3).

Other ABEAM components within the scope of this invention may comprise those portions of any molecule known to bind to the anion binding exosite of thrombin. These include amino acids 1675-1686 of Factor V, amino acids 272-285 of platelet glycoprotein Ib, amino acids 415-428 of thrombomodulin, amino acids 245-259 of prothrombin Fragment 2 and amino acids 30 to 44 of fibrinogen Aα chain. In addition, the ABEAM component may be selected from any of the hirudin peptide analogues described by J. L. Krstenansky et al., "Development of MDL-28,050, A Small Stable Antithrombin Agent Based On A Functional Domain of the Leech Protein, Hirudin", *Thromb. Haemostas.*, 63, pp. 208-14 (1990) or those described by J. L. Krstenansky et al., "Hirudin and Hirullin C-Terminal Domains: Structural Comparisons and Antithrombin Properties", Abstract, *Circulation*, 82, p. II-659 (1990).

The structure and synthesis of a wide variety of thrombin inhibitory domains that may be utilized in the bifunctional inhibitors of this invention are described in copending U.S. application Ser. No. 549,388, the disclosure of which is herein incorporated by reference.

According to a preferred embodiment, the bifunctional inhibitor of this invention is a polypeptide comprising the amino acid sequence (SEQ ID NO:2):

Gly—Pro—Arg—Pro—Gly—Gly—Gly—Gly—Asn—Gly—
Asp—Phe—Glu—Glu—Ile—Pro—Glu—Glu—Tyr—Leu—
Gly—Gly—Gly—Gly—Glu—Ala—Gly—Glu—Glu—Cys—
Asp—Cys—Gly—Ser—Pro—Glu—Asn—Pro—Cys—Asp—
Asp—Ala—Ala—Thr—Cys—Lys—Leu—Arg—Pro—Gly—
Ala—Gln—Cys—Ala—Glu—Gly—Leu—Cys—Cys—Asp—
Gln—Cys—Lys—Phe—Xaa—Lys—Glu—Gly—Thr—Val—
Cys—Arg—Arg—Ala—Arg—Gly—Asp—Asp—Val—Asn—
Asp—Tyr—Cys—Asn—Gly—Ile—Ser—Ala—Gly—Cys—
Pro—Arg—Asn—Pro—Phe—His, or a polypeptide comprising the amino acid sequence (SEQ ID NO:3):

Glu—Ala—Gly—Glu—Glu—Cys—Asp—Cys—Gly—Ser—
Pro—Glu—Asn—Pro—Cys—Asp—Asp—Ala—Ala—Thr—
Cys—Lys—Leu—Arg—Pro—Gly—Ala—Gln—Cys—Ala—

-continued
Glu—Gly—Leu—Cys—Cys—Asp—Gln—Cys—Lys—Phe—
Xaa—Lys—Glu—Gly—Thr—Val—Cys—Arg—Arg—Ala—
Arg—Gly—Asp—Asp—Val—Asn—Asp—Tyr—Cys—Asn—
Gly—Ile—Ser—Ala—Gly—Cys—Pro—Arg—Asn—Pro—
Phe—His—Gly—Gly—Gly—Gly—Gly—Pro—Arg—Pro—
Gly—Gly—Gly—Gly—Asn—Gly—Asp—Phe—Glu—Glu—
Ile—Pro—Glu—Glu—Tyr—Leu, wherein Xaa is any amino acid. The preferred inhibitors of this invention are termed "appilogs". The most preferred bifunctional inhibitors of the present invention consist of SEQ ID NO:4:

Gly—Ser—Ile—Glu—Gly—Arg—Pro—Glu—Phe—Met—
Gly—Pro—Arg—Pro—Gly—Gly—Gly—Gly—Asn—Gly—
Asp—Phe—Glu—Glu—Ile—Pro—Glu—Glu—Tyr—Leu—
Gly—Gly—Gly—Gly—Glu—Ala—Gly—Glu—Glu—Cys—
Asp—Cys—Gly—Ser—Pro—Glu—Asn—Pro—Cys—Asp—
Asp—Ala—Ala—Thr—Cys—Lys—Leu—Arg—Pro—Gly—
Ala—Gln—Cys—Ala—Glu—Gly—Leu—Cys—Cys—Asp—
Gln—Cys—Lys—Phe—Met—Lys—Glu—Gly—Thr—Val—
Cys—Arg—Arg—Ala—Arg—Gly—Asp—Asp—Val—Asn—
Asp—Tyr—Cys—Asn—Gly—Ile—Ser—Ala—Gly—Cys—
Pro—Arg—Asn—Pro—Phe—His, termed "Gly-Ser-Ile-Glu-Gly-Arg-Pro-Glu-Phe-Met-N-appilog"; amino acids 11-106 of SEQ ID NO:4:

Gly—Pro—Arg—Pro—Gly—Gly—Gly—Gly—Asn—
Gly—Asp—Phe—Glu—Glu—Ile—Pro—Glu—Glu—
Tyr—Leu—Gly—Gly—Gly—Gly—Glu—Ala—Gly—
Glu—Glu—Cys—Asp—Cys—Gly—Ser—Pro—Glu—
Asn—Pro—Cys—Asp—Asp—Ala—Ala—Thr—Cys—
Lys—Leu—Arg—Pro—Gly—Ala—Gln—Cys—Ala—
Glu—Gly—Leu—Cys—Cys—Asp—Gln—Cys—Lys—
Phe—Met—Lys—Glu—Gly—Thr—Val—Cys—Arg—
Arg—Ala—Arg—Gly—Asp—Asp—Val—Asn—Asp—
Tyr—Cys—Asn—Gly—Ile—Ser—Ala—Gly—Cys—
Pro—Arg—Asn—Pro—Phe—His, termed "N-appilog"; amino acids 10-106 of SEQ ID NO:4:

Met—Gly—Pro—Arg—Pro—Gly—Gly—Gly—Gly—Asn—
Gly—Asp—Phe—Glu—Glu—Ile—Pro—Glu—Glu—Tyr—
Leu—Gly—Gly—Gly—Gly—Glu—Ala—Gly—Glu—Glu—
Cys—Asp—Cys—Gly—Ser—Pro—Glu—Asn—Pro—Cys—
Asp—Asp—Ala—Ala—Thr—Cys—Lys—Leu—Arg—Pro—
Gly—Ala—Gln—Cys—Ala—Glu—Gly—Leu—Cys—Cys—
Asp—Gln—Cys—Lys—Phe—Met—Lys—Glu—Gly—Thr—
Val—Cys—Arg—Arg—Ala—Arg—Gly—Asp—Asp—Val—
Asn—Asp—Tyr—Cys—Asn—Gly—Ile—Ser—Ala—Gly—
Cys—Pro—Arg—Asn—Pro—Phe—His, termed "Met-N-appilog"; SEQ ID NO:5:

Ala—Asn—Ser—Gly—Pro—Arg—Pro—Gly—Gly—Gly—
Gly—Asn—Gly—Asp—Phe—Glu—Glu—Ile—Pro—Glu—
Glu—Tyr—Leu—Gly—Gly—Gly—Gly—Glu—Ala—Gly—
Glu—Glu—Cys—Asp—Cys—Gly—Ser—Pro—Glu—Asn—
Pro—Cys—Asp—Asp—Ala—Ala—Thr—Cys—Lys—Leu—
Arg—Pro—Gly—Ala—Gln—Cys—Ala—Glu—Gly—Leu—
Cys—Cys—Asp—Gln—Cys—Lys—Phe—Met—Lys—Glu—
Gly—Thr—Val—Cys—Arg—Arg—Ala—Arg—Gly—Asp—
Asp—Val—Asn—Asp—Tyr—Cys—Asn—Gly—Ile—Ser—
Ala—Gly—Cys—Pro—Arg—Asn—Pro—Phe—His, termed "Ala-Asn-Ser-N-appilog"; SEQ ID NO:6:

Ile—Met—Gly—Pro—Arg—Pro—Gly—Gly—Gly—Gly—
Asn—Gly—Asp—Phe—Glu—Glu—Ile—Pro—Glu—Glu—
Tyr—Leu—Gly—Gly—Gly—Gly—Glu—Ala—Gly—Glu—
Glu—Cys—Asp—Cys—Gly—Ser—Pro—Glu—Asn—Pro—
Cys—Asp—Asp—Ala—Ala—Thr—Cys—Lys—Leu—Arg—
Pro—Gly—Ala—Gln—Cys—Ala—Glu—Gly—Leu—Cys—

-continued

Cys—Asp—Gln—Cys—Lys—Phe—Leu—Lys—Glu—Gly—
Thr—Val—Cys—Arg—Arg—Ala—Arg—Gly—Asp—Asp—
Val—Asn—Asp—Tyr—Cys—Asn—Gly—Ile—Ser—Ala—
Gly—Cys—Pro—Arg—Asn—Pro—Phe—His, termed "Ile-Met-N-appilog(Leu$_{65}$)"; amino acids 3-98 of SEQ ID NO:6:

Gly—Pro—Arg—Pro—Gly—Gly—Gly—Gly—Asn—Gly—
Asp—Phe—Glu—Glu—Ile—Pro—Glu—Glu—Tyr—Leu—
Gly—Gly—Gly—Gly—Glu—Ala—Gly—Glu—Glu—Cys—
Asp—Cys—Gly—Ser—Pro—Glu—Asn—Pro—Cys—Asp—
Asp—Ala—Ala—Thr—Cys—Lys—Leu—Arg—Pro—Gly—
Ala—Gln—Cys—Ala—Glu—Gly—Leu—Cys—Cys—Asp—
Gln—Cys—Lys—Phe—Leu—Lys—Glu—Gly—Thr—Val—
Cys—Arg—Arg—Ala—Arg—Gly—Asp—Asp—Val—Asn—
Asp—Tyr—Cys—Asn—Gly—Ile—Ser—Ala—Gly—Cys—
Pro—Arg—Asn—Pro—Phe—His, termed "N-appilog(Leu$_{65}$)"; SEQ ID NO:7:

Gly—Ser—Ile—Glu—Gly—Arg—Pro—Glu—Phe—Met—
Glu—Ala—Gly—Glu—Glu—Cys—Asp—Cys—Gly—Ser—
Pro—Glu—Asn—Pro—Cys—Asp—Asp—Ala—Ala—Thr—
Cys—Lys—Leu—Arg—Pro—Gly—Ala—Gln—Cys—Ala—
Glu—Gly—Leu—Cys—Cys—Asp—Gln—Cys—Lys—Phe—
Met—Lys—Glu—Gly—Thr—Val—Cys—Arg—Arg—Ala—
Arg—Gly—Asp—Asp—Val—Asn—Asp—Tyr—Cys—Asn—
Gly—Ile—Ser—Ala—Gly—Cys—Pro—Arg—Asn—Pro—
Phe—His—Gly—Gly—Gly—Gly—Pro—Arg—Pro—
Gly—Gly—Gly—Asn—Gly—Asp—Phe—Glu—Glu—
Ile—Pro—Glu—Glu—Tyr—Leu, termed "Gly-Ser-Ile-Glu-Gly-Arg-Pro-Glu-Phe-Met-C-appilog"; amino acids 11-106 of SEQ ID NO:7:

Glu—Ala—Gly—Glu—Glu—Cys—Asp—Cys—Gly—Ser—
Pro—Glu—Asn—Pro—Cys—Asp—Asp—Ala—Ala—Thr—
Cys—Lys—Leu—Arg—Pro—Gly—Ala—Gln—Cys—Ala—
Glu—Gly—Leu—Cys—Cys—Asp—Gln—Cys—Lys—Phe—
Met—Lys—Glu—Gly—Thr—Val—Cys—Arg—Arg—Ala—
Arg—Gly—Asp—Asp—Val—Asn—Asp—Tyr—Cys—Asn—
Gly—Ile—Ser—Ala—Gly—Cys—Pro—Arg—Asn—Pro—
Phe—His—Gly—Gly—Gly—Gly—Pro—Arg—Pro—
Gly—Gly—Gly—Asn—Gly—Asp—Phe—Glu—Glu—
Ile—Pro—Glu—Glu—Tyr—Leu, termed "C-appilog"; amino acids 10-106 of SEQ ID NO:7:

Met—Glu—Ala—Gly—Glu—Glu—Cys—Asp—Cys—Gly—
Ser—Pro—Glu—Asn—Pro—Cys—Asp—Asp—Ala—Ala—
Thr—Cys—Lys—Leu—Arg—Pro—Gly—Ala—Gln—Cys—
Ala—Glu—Gly—Leu—Cys—Cys—Asp—Gln—Cys—Lys—
Phe—Met—Lys—Glu—Gly—Thr—Val—Cys—Arg—Arg—
Ala—Arg—Gly—Asp—Asp—Val—Asn—Asp—Tyr—Cys—
Asn—Gly—Ile—Ser—Ala—Gly—Cys—Pro—Arg—Asn—
Pro—Phe—His—Gly—Gly—Gly—Gly—Pro—Arg—
Pro—Gly—Gly—Gly—Asn—Gly—Asp—Phe—Glu—
Glu—Ile—Pro—Glu—Glu—Tyr—Leu, termed "Met-C-appilog"; SEQ ID NO:8:

Ala—Asn—Ser—Glu—Ala—Gly—Glu—Glu—Cys—Asp—
Cys—Gly—Ser—Pro—Glu—Asn—Pro—Cys—Asp—Asp—
Ala—Ala—Thr—Cys—Lys—Leu—Arg—Pro—Gly—Ala—
Gln—Cys—Ala—Glu—Gly—Leu—Cys—Cys—Asp—Gln—
Cys—Lys—Phe—Met—Lys—Glu—Gly—Thr—Val—Cys—
Arg—Arg—Ala—Arg—Gly—Asp—Asp—Val—Asn—Asp—
Tyr—Cys—Asn—Gly—Ile—Ser—Ala—Gly—Cys—Pro—
Arg—Asn—Pro—Phe—His—Gly—Gly—Gly—Gly—Gly—
Pro—Arg—Pro—Gly—Gly—Gly—Gly—Asn—Gly—Asp—
Phe—Glu—Glu—Ile—Pro—Glu—Glu—Tyr—Leu, termed "Ala-Asn-Ser-C-appilog"; SEQ ID NO:9:

Ile—Met—Glu—Ala—Gly—Glu—Glu—Cys—Asp—Cys—
Gly—Ser—Pro—Glu—Asn—Pro—Cys—Asp—Asp—Ala—
Ala—Thr—Cys—Lys—Leu—Arg—Pro—Gly—Ala—Gln—
Cys—Ala—Glu—Gly—Leu—Cys—Cys—Asp—Gln—Cys—
Lys—Phe—Leu—Lys—Glu—Gly—Thr—Val—Cys—Arg—
Arg—Ala—Arg—Gly—Asp—Asp—Val—Asn—Asp—Tyr—
Cys—Asn—Gly—Ile—Ser—Ala—Gly—Cys—Pro—Arg—
Asn—Pro—Phe—His—Gly—Gly—Gly—Gly—Gly—Pro—
Arg—Pro—Gly—Gly—Gly—Gly—Asn—Gly—Asp—Phe—
Glu—Glu—Ile—Pro—Glu—Glu—Tyr—Leu, termed "Ile-Met-C-appilog(Leu$_{41}$)"; and amino acids 3-98 of SEQ ID NO:9:

Glu—Ala—Gly—Glu—Glu—Cys—Asp—Cys—Gly—Ser—
Pro—Glu—Asn—Pro—Cys—Asp—Asp—Ala—Ala—Thr—
Cys—Lys—Leu—Arg—Pro—Gly—Ala—Gln—Cys—Ala—
Glu—Gly—Leu—Cys—Cys—Asp—Gln—Cys—Lys—Phe—
Leu—Lys—Glu—Gly—Thr—Val—Cys—Arg—Arg—Ala—
Arg—Gly—Asp—Asp—Val—Asn—Asp—Tyr—Cys—Asn—
Gly—Ile—Ser—Ala—Gly—Cys—Pro—Arg—Asn—Pro—
Phe—His—Gly—Gly—Gly—Gly—Gly—Pro—Arg—Pro—
Gly—Gly—Gly—Gly—Asn—Gly—Asp—Phe—Glu—Glu—
Ile—Pro—Glu—Glu—Tyr—Leu, termed "C-appilog(Leu$_{41}$)".

The designations "N-" and "C-" in the names of these preferred polypeptides refer to the location of the thrombin inhibitory domain relative to the glycoprotein IIb/IIIa inhibitory domain.

The bifunctional inhibitors of the present invention may be synthesized by various techniques which are well known in the art. These include isolation of the two separate domains from natural or recombinant sources followed by fusion or crosslinking, recombinant DNA techniques, solid-phase peptide synthesis, solution-phase peptide synthesis, organic chemical synthesis techniques, or a combination of these techniques. The choice of technique will, of course, depend upon the actual composition of the particular bifunctional inhibitor. In a preferred embodiment of this invention, the bifunctional inhibitor is encoded by a synthetic gene and expressed as part of a fusion protein.

The present invention also relates to DNA sequences which encode the preferred inhibitors of this invention. Because these polypeptides are novel and not found in nature, the genes which encode them must be synthesized by chemical means using an oligonucleotide synthesizer. Such oligonucleotides are designed based on the disclosed amino acid sequence of these preferred inhibitors.

Standard methods may be applied to synthesize a gene encoding an appilog. For example, the complete amino acid sequence may be used to construct a back-translated gene. A DNA oligomer containing a nucleotide sequence capable of coding for an appilog may be synthesized in a single step. Alternatively, several smaller oligonucleotides coding for portions of an appilog polypeptide may be synthesized and subsequently ligated together. Preferably, an appilog gene is synthesized as 10-20 separate oligonucleotides which are subsequently linked together. The individual oligonucleotides contain 5' or 3' overhangs for complementary assembly.

A synthetic gene coding for applaggin, an antiplatelet polypeptide from the venom of *Agkistrodon p. piscivorus*, has previously been described in PCT application No. WO 90/08772. Therefore, the construction of an appilog gene may alternatively be achieved by constructing a DNA sequence encoding the thrombin inhibitory domain and ligating it to the 5' or 3' end of the applaggin gene. The DNA sequence coding for the thrombin inhibitory domain is preferably synthesized as 3 pairs of partially complementary oligonucleotides containing 5' and/or 3' overhangs for complementary assembly. It will be apparent to those of skill in the art that the pairs of oligonucleotide will be slightly different depending on whether the final desired construct contains this domain at the N- or C-terminus. This is because the amino acid structure of the thrombin inhibitory domain is different in the two polypeptides.

Once assembled, the gene will be characterized by sequences which are recognized by restriction endonucleases, including unique restriction sites for direct assembly into a cloning or an expression vector; preferential codons based upon the host expression system to be used; and a sequence which, when transcribed, produces a mRNA with minimal secondary structure. Proper assembly may be confirmed by nucleotide sequencing, restriction mapping, and expression of a biologically active polypeptide in a suitable host.

The DNA sequence according to this invention comprises the nucleic acid sequence (SEQ ID NO:10):

```
GGT CCG CGT CCG GGT GGT GGT GGT AAC GGT GAC
TTC GAA GAA ATC CCG GAA GAA TAC CTG GGT GGT
GGT GGT GAA GCT GGT GAA GAA TGC GAC TGC GGA
TCC CCG GAA AAC CCG TGC GAC GAC GCT GCT ACC
TGC AAA CTG CGT CCG GGT GCT CAG TGC GCT GAA
GGT CTG TGC TGC GAC CAG TGC AAA TTC NNN AAA
GAA GGT ACC GTT TGC CGT CGT GCT CGT GGT GAC
GAC GTT AAC GAC TAC TGC AAC GGT ATC TCT GCA
GGT TGC CCG CGT AAC CCG TTC CAC,
``` or (SEQ ID NO:11):

```
GAA GCT GGT GAA GAA TGC GAC TGC GGA TCC CCG
GAA AAC CCG TGC GAC GAC GCT GCT ACC TGC AAA
CTG CGT CCG GGT GCT CAG TGC GCT GAA GGT CTG
TGC TGC GAC CAG TGC AAA TTC NNN AAA GAA GGT
ACC GTT TGC CGT CGT GCT CGT GGT GAC GAC GTT
AAC GAC TAC TGC AAC GGT ATC TCT GCA GGT TGC
CCG CGT AAC CCG TTC CAC GGT GGT GGT GGT GGT
CCG CGT CCG GGT GGT GGT GGT AAC GGT GAC TTC
GAA GAA ATC CCG GAA GAA TAC CTG,
``` wherein each N, either the same or different, is any nucleotide. It will be understood by those of skill in the art that, due to the degeneracy of the genetic code, DNA molecules comprising many other nucleotide sequences will also be capable of encoding the preferred inhibitors of this invention. It will also be apparent that many of these DNAs will be faithfully expressed in hosts transformed with them. Therefore, the present invention relates not only to DNA molecules comprising the nucleotide sequences specifically set forth above, but to all DNA molecules comprising a DNA sequence which encodes the same amino acid sequence and which can be expressed by one or more hosts transformed with them.

The present invention also relates to recombinant DNA molecules comprising the above DNA sequences. Preferably, the recombinant DNA molecules of this invention will be capable of directing expression of the preferred inhibitors of this invention in hosts transformed therewith. As such, the DNA sequence encoding the preferred inhibitors of the invention must be operatively linked to an expression control sequence. The term "operatively linked", as used herein refers to a positioning in a vector so that transcription and translation of the coding sequence is directed by the control sequence.

To construct the recombinant DNA molecules of this invention, the DNA sequences of this invention may be inserted into and expressed using a wide variety of vectors. Furthermore, within each specific expression vector, various sites may be selected for insertion of these DNA sequences. These sites are usually designated by the restriction endonuclease which cuts them. They are well recognized by those of skill in the art. It is, of course, to be understood that an expression vector useful in this invention need not have a restriction endonuclease site for insertion of the chosen DNA fragment. Instead, the vector may be joined to the fragment by alternative means.

The expression vector, and in particular the site chosen therein for insertion of a selected DNA fragment and its operative linking therein to an expression control sequence, is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Useful expression vectors for eukaryotic hosts include, for example, vectors comprising expression control sequences from SV40, bovine papilloma virus, adenovirus and cytomegalovirus; and vectors useful specifically in insect cells, such as pVL 941. Useful bacterial expression vectors include known bacterial plasmids, e.g., plasmids from *E. coli* including colEl, pCRl, pBR322, pMB9 and their derivatives; wider host range plasmids, such as RP4; the numerous derivatives of λ phage, e.g., NM 989 and the λ gt series; other DNA phages, e.g., M13 and other Filamentous single-stranded DNA phages; and commercially available high expression vectors, e.g., the pGEM series and the lambda Zap vectors. Vectors useful in yeasts include the 2μ plasmid and derivatives thereof.

Such expression vectors are also characterized by at least one expression control sequence. When the DNA sequences of this invention are inserted in the vector they should be operatively linked to such expression control sequence in order to control and to regulate the expression of that cloned DNA sequence. Examples of useful expression control sequences include the malE system, the OmpA system, the lac system, the trp system, the tac system, the trc system, major operator and promoter regions of phage λ, the control region of fd coat protein, the glycolytic promoters of yeast, e.g., the promoter for 3-phosphoglycerate kinase, the promoters of yeast acid phosphatase, e.g., Pho5, the promoters of the yeast-mating factors, and promoters derived from polyoma, adenovirus, retrovirus, and simian virus, e.g., the early and late promoters of SV40, and other sequences known to control the expression of genes of prokaryotic or eukaryotic cells and their viruses or combinations thereof.

The recombinant DNA molecules of the present invention may also comprise other DNA coding sequences fused to and in frame with the DNA sequences encoding the preferred inhibitors of this invention. For example, a DNA sequence encoding a bacterial or eukaryotic signal sequence may be fused to the 5' end of the appilog DNA sequence. This would allow the expressed product to be either secreted or targeted to a specific subcellular compartment within the host cell. And most signal sequences are removed by the hose cell after performing their targeting function, thus obviating the need for their in vitro removal after purification of the desired polypeptide. Many signal sequences, as well as the DNA sequences encoding them are known in the art. The fusion of such signal sequence DNA to and in frame with the appilog DNA sequences of this invention can be achieved by standard molecular biology techniques.

According to a preferred embodiment, the recombinant DNA molecules of this invention comprise an OmpA signal sequence DNA fused to and in frame with an appilog DNA sequence. When such a fusion protein is expressed in a bacterial host it is secreted into the periplasmic space with concomitant removal of the OmpA signal.

Alternatively, an appilog DNA sequence of this invention may be expressed as a fusion protein by inframe ligation to a second DNA sequence encoding a host cell polypeptide. The expression of a fusion protein may afford several advantages, such as increased resistance to host cell degradation, ease of identification based upon the activity or antigenicity of the hose cell polypeptide portion and ease of purification, based upon the physical or immunological properties of the hose cell polypeptide portion.

According to a preferred embodiment, the recombinant DNA molecule of this invention comprises a DNA sequence encoding a protein having the formula:

$Z_1$-$Z_2$-$Z_3$-$Z_4$, wherein $Z_1$ is hydrogen or the amino acid sequence of the maltose binding protein signal sequence, $Z_2$ is the amino acid sequence of the maltose binding protein, $Z_3$ is a bond or from 1 to 12 residues, either the same or different, of any amino acid, and $Z_4$ is the amino acid sequence of N- or C-appilog.

The DNA sequence of the malE gene, which encodes the maltose binding protein and its signal sequence is known in the art [P. Duplay et al., *J. Biol. Chem.*, 259, pp. 10606-13 (1984)]. Expression vectors comprising the malE gene have also been previously described [P. D. Riggs, "Expression and Purification of Maltose-Binding Protein Fusions", in *Current Protocols in Molecular Biology*, F. M. Ausubel et al., eds., John Wiley & sons, New York, vol. 2, pp. 16.6.1-16.6.12 (1990)]. The advantage of encoding a maltose binding protein-appilog fusion protein is two fold. First, the expressed fusion protein is easily purified by affinity chromatography using an amylose resin which specifically binds maltose binding protein [C.-d. Guan et al., "Vectors That Facilitate the Expression and Purification of Foreign Peptides in *Escherichia coli* by Fusion to Maltose-Binding Protein", *Gene*, 67, pp. 21-30 (1988)].

Second, the fusion protein contains a four amino acid Factor Xa cleavage site located at the junction between the maltose binding protein and the appilog, thus allowing easy removal of the maltose binding protein portion from the desired appilog.

According to this embodiment, when $Z_1$ is the maltose binding protein signal sequence, the fusion protein expressed in a bacterial host is targeted to the periplasm. When $Z_1$ is hydrogen, the expressed fusion protein will remain in the bacterial host cell cytoplasm.

According to another embodiment of this invention, if amino acid Xaa of the malE-appilog fusion protein is any amino acid except methionine, cyanogen bromide treatment may replace Factor Xa digestion in the process for producing an appilog. As is well known in the art, cyanogen bromide cleaves at the C-terminal side of methionine residues. It will therefore be apparent that such treatment will produce an appilog without any additional N-terminal amino acids (as opposed to Factor Xa treatment which produces an appilog having from 2 to 10 extra amino terminal amino acids, depending on the construction). According to this embodiment the most preferred appilogs are N-appilog(Leu$_{65}$) (wherein amino acid Xaa, which is residue number 65, is leucine) and C-appilog(Leu$_{41}$) (wherein amino acid Xaa, which is residue number 41, is leucine).

The invention also relates to hosts transformed with the recombinant DNA molecules described above. Useful hosts which may be transformed with these recombinant DNA molecules and which may be employed to express the bifunctional inhibitors of this invention may include well known eukaryotic and prokaryotic hosts, such as strains of *E. coli*, i.e., *E. coli* SG-936, *E. coli* HB 101, *E. coli* W3110, *E. coli* X1776, *E. coli* X2282, *E. coli* DHI, *E. coli* DH5-alpha and *E. coli* MRC1; Pseudomonas; Bacillus, such as *Bacillus subtilis*; Streptomyces; yeasts and other fungi; animal cells, such as COS cells, CHO cells, human cells, insect cells, such as *Spodoptera frugiperda* (SF9); and plant cells in tissue culture.

Of course, it will be understood that not all host/expression vector combinations will function with equal efficiency in expressing the DNA sequences of this invention or in producing the bifunctional inhibitors of this invention. However, a particular selection of a host-expression vector combination may be made by those of skill in the art, after due consideration of the principles set forth herein without departing from the scope of this invention. For example, the selection should be based on a balancing of a number of factors. These include, for example, compatibility of the hose and vector, toxicity of the proteins encoded by the DNA sequence to the host, vector copy number and the ability to control that copy number, the expression of other proteins encoded by the vector, such as antibiotic markers, ease of recovery of the desired protein, expression characteristics of the DNA sequences and the expression control sequences operatively linked to them, biosafety, costs and the folding, form or any other necessary post-expression modifications of the desired protein.

The bifunctional inhibitors of the present invention display potent anti-thrombin and anti-platelet activity. These activities may be assayed in vitro using any conventional technique. Preferably, the anti-thrombin assay involves direct determination of the thrombin-inhibitory activity of the molecule. Such techniques measure the inhibition of thrombin-catalyzed cleavage of colorimetric substrates or, more preferably, the increase in thrombin times or increase in activated partial thromboplastin times of human plasma. The latter assay measures factors in the "intrinsic" pathway of coagulation. Alternatively, the assay employed may use purified thrombin and fibrinogen to measure the inhibition of release of fibrinopeptides A or B by radioimmunoassay or ELISA.

The antiplatelet activity of the molecules of this invention may also be measured by any of a number of conventional platelet assays. Preferably, the assay will measure a change in the degree of aggregation of platelets or a change in the release of a platelet secretory component in the presence of platelet activator. The former may be measured in an aggregometer. The latter may be measured using RIA or ELISA techniques specific for the secreted component.

The bifunctional inhibitors of the present invention may be formulated into pharmaceutically acceptable compositions for inhibiting both thrombin- and platelet mediated functions in a patient or in extracorporeal blood. As used in this application, the term "extracorporeal blood" includes blood removed in line from a patient, subjected to extracorporeal treatment, and returned to the patient in processes such as dialysis procedures or blood filtration or blood bypass during surgery. The term also includes blood products which are stored extracorporeally for eventual administration to a patient. Such products include whole blood, platelet concentrates and any other blood fraction in which inhibition of both platelet activation and thrombin is desired.

The bifunctional inhibitors of the present invention are also useful in compositions and methods for the treatment and prophylaxis of various diseases and pathological states attributed to functions and processes mediated by thrombin and/or platelets. These include thrombotic diseases, such as myocardial infarction, stroke, pulmonary embolism, deep vein thrombosis and peripheral arterial occlusion; restenosis following arterial injury or invasive cardiological procedures; acute or chronic atherosclerosis; edema and inflammation; abnormal cell regulatory processes (e.g. secretion, shape changes, proliferation); cancer and metastasis; and neurodegenerative diseases.

According to an alternate embodiment of the present invention, the bifunctional inhibitors may be employed in compositions and methods for decreasing reperfusion or increasing reocclusion time in a patient. These compositions may additionally comprise a pharmaceutically effective amount of a thrombolytic agent.

Thrombolytic agents which may be employed in the compositions of the present invention are those known in the art. Such agents include, but are not limited to, tissue plasminogen activator purified from natural sources, recombinant tissue plasminogen activator, streptokinase, urokinase, prourokinase, anisolated streptokinase plasminogen activator complex (ASPAC), animal salivary gland plasminogen activators and known, biologically active derivatives of any of the above.

In these compositions, the bifunctional inhibitor and the thrombolytic agent work in a complementary fashion to dissolve blood clots, resulting in decreased reperfusion times and increased reocclusion times in patients treated with them. Specifically, the thrombolytic agent dissolves the clot, while the bifunctional inhibitor prevents newly exposed, clot-entrapped or clot-bound thrombin, as well as platelets present at the clot site, from regenerating the clot. The use of the bifunctional inhibitor in the compositions of this invention advantageously allows the administration of a thrombolytic reagent in dosages previously considered too low to result in thrombolytic effects if given alone. This avoids some of the undesirable side effects associated with the use of thrombolytic agents, such as bleeding complications.

The dosage and dose rate of the bifunctional inhibitor of this invention will depend on a variety of factors, such as the size of the patient, the specific pharmaceutical composition used, the object of the treatment, i.e., therapy or prophylaxis, the nature of the thrombotic disease to be treated, and the judgment of the treating physician. A pharmaceutically effective amount of a bifunctional inhibitor of this invention will normally be in the dosage range of between about 0.001–500 mg/kg body weight, preferably about 0.1–50 mg/kg body weight. For the treatment of extracorporeal blood, the bifunctional inhibitors of the present invention should be used at about 0.005–50 µg/ml, preferably at about 0.5–5 µg/ml of extracorporeal blood. It should be understood that other dosages outside of these illustrative ranges may be employed in the pharmaceutical compositions of this invention.

In compositions containing a thrombolytic agent, a pharmaceutically effective dose of the thrombolytic agent is between about 10% and 80% of the conventional dosage range. The "conventional dosage range" of a thrombolytic agent is the daily dosage used when that agent is employed in a monotherapy. [*Physician's Desk Reference* 1989, 43rd Edition, Edward R. Barnhart, publisher]. That conventional dosage range will, of course, vary depending on the thrombolytic agent employed. Examples of conventional dosage ranges are as follows: urokinase — 500,000 to 6,250,000 units/patient; streptokinase — 140,000 to 2,500,000 units/patient; tPA — 0.5 to 5.0 mg/kg body weight; ASPAC — 0.1 to 10 units/kg body weight.

Once improvement in the patient's condition has occurred, a maintenance dose of a composition of this invention is administered, if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment upon any recurrence of disease symptoms.

The pharmaceutically acceptable compositions of the present invention preferably include at least one pharmaceutically acceptable carrier. In addition, the pharmaceutically acceptable compositions of the present invention also comprise a pharmaceutically acceptable buffer, preferably phosphate buffered saline, together with a pharmaceutically acceptable compound for adjusting isotonic pressure, such as sodium chloride, mannitol or sorbitol.

Various dosage forms may be employed to administer the compositions and combinations of this invention. These include, but are not limited to, parenteral administration, oral administration and topical application. The compositions and combinations of this invention may be administered to the patient in any pharmaceutically acceptable dosage form, including those which may be administered to a patient intravenously as bolus or by continued infusion, intramuscularly — including paravertebrally and periarticularly — subcutaneously, intracutaneously, intra-articularly, intrasynovially, intrathecally, intra-lesionally, periostally or by oval, nasal, or topical routes. Such compositions and combinations are preferably adapted for topical, nasal, oral and parenteral administration, but, most preferably, are formulated for parenteral administration.

Parenteral compositions are most preferably administered intravenously either in a bolus form or as a constant infusion. If the thrombin inhibitor is being used as an antiplatelet compound, constant infusion is preferred. If the thrombin inhibitor is being used as an anticoagulant, a subcutaneous or intravenous bolus injection is preferred. For parenteral administration, fluid unit dose forms are prepared which contain a thrombin inhibitor of the present invention and a sterile vehicle. The thrombin inhibitor may be either suspended or dissolved, depending on the nature of the vehicle and the nature of the particular thrombin inhibitor. Parenteral compositions are normally prepared by dissolving the thrombin inhibitor in a vehicle, optionally together with other components, and filter sterilizing before filling into a suitable vial or ampule and sealing. Preferably, adjuvants such as a local anesthetic, preservatives and buffering agents are also dissolved in the vehicle. The composition may then be frozen and lyophilized to enhance stability.

Parenteral suspensions are prepared in substantially the same manner, except that the active component is suspended rather than dissolved in the vehicle. Sterilization of the compositions is preferably achieved by exposure to ethylene oxide before suspension in the sterile vehicle. Advantageously, a surfactant or wetting agent is included in the composition to facilitate uniform distribution of its components.

Tablets and capsules for oral administration may contain conventional excipients, such as binding agents, fillers, diluents, tableting agents, lubricants, disintegrants, and wetting agents. The tablet may be coated according to methods well known in the art. Suitable fillers which may be employed include cellulose, mannitol, lactose and other similar agents. Suitable disintegrants include, but are not limited to, starch, polyvinylpyrrolidone and starch derivatives, such as sodium starch glycolate. Suitable lubricants include, for example, magnesium stearate. Suitable wetting agents include sodium lauryl sulfate.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives. These include suspending agents; such as sorbitol, syrup, methyl cellulose, gelatin, hydroxyethylcellulose, carboxymethylcellulose, aluminum stearate gel or hydrogenated edible fats; emulsifying agents which include lecithin, sorbitan monooleate, polyethylene glycols, or acacia; non-aqueous vehicles, such as almond oil, fractionated coconut oil, and oily esters; and preservatives, such as methyl or propyl p-hydroxybenzoate or sorbic acid.

Compositions formulated for topical administration may, for example, be in aqueous jelly, oily suspension or emulsified ointment form.

This invention also relates to methods employing the bifunctional inhibitors of this invention in the treatment of tumor metastases. The treatment of tumor metastases is manifested by the inhibition of different facets of metastatic cell growth by the two different inhibitory domains of the bifunctional inhibitor. The thrombin inhibitory domain counteracts a procoagulant enzyme present in many cancer cells. This enzyme activates the conversion of Factor X to Factor Xa in the coagulation cascade, resulting in fibrin deposition which, in turn, serves as a substrate for tumor growth. By inhibiting thrombin, fibrin deposition is decreased, thus decreasing the sites upon which tumor cells may grow.

The glycoprotein IIb/IIIa inhibitory domain inhibits the binding of tumor cells to cell matrix proteins. It has previously been shown that Arg-Gly-Asp-containing peptides and polypeptides inhibit the binding of tumor cells to fibronectin and vitronectin [M. J. Humphries et al., "Investigation of the Biological Effects of Anti-Cell Adhesive Synthetic Peptides that Inhibit Experimental Metastasis of B16F10 Murine Myeloma Cells", *J. Clin. Invest.*, 81, p. 782 (1988)]. And trigramin has been shown to inhibit the adhesion of human melanoma cells to a fibronectin matrix [K. A. Knudsen et al., "Trigramin, An RGD-Containing Peptide from Snake Venom, Inhibits Cell-Substratum Adhesion of Human Melanoma Cells", *Exp. Cell. Res.*, 179, pp. 42–49 (1988)]. As described herein, the preferred glycoprotein IIb/IIIa domain comprises an Arg-Gly-Asp sequence. Therefore, it will inhibit cancer cell binding to extracellular matrix. It can be readily seen that the bifunctional inhibitors of this invention may serve to interrupt both metastatic cell-mediated deposition of fibrin and the binding of metastatic cells to extracellular matrix. Each of these inhibitory functions can decrease metastatic cell growth. Accordingly, the molecules of this invention may be employed in the treatment of cancer.

In order that this invention may be more fully understood, the following examples are set forth. It should be understood that these examples are for illustrative purposes only and are not to be construed as limiting this invention in any manner.

Unless otherwise indicated, all restriction digests described in the following examples were performed for 2 hours at 37° C. using restriction enzymes obtained from New England Biolabs (Beverly, Mass.) in the manufacturer's recommended buffer. All other standard molecular biology procedures, such as kinasing, ligation, transfections, plasmid preparation, DNA extractions, ethanol precipitations, agarose gel electrophoresis, electroelution, etc. were performed as described in T. Maniatis et al., *Molecular Cloning — A Laboratory Manual*, Cold Spring Harbor Laboratory (1982).

EXAMPLE 1

Synthesis Of Appilog Genes

A synthetic gene encoding applaggin, an antiplatelet polypeptide from the snake *Agkistrodon p. piscivorus* has previously been described in WO 90/08772. The gene was designed using the complete amino acid sequence of the natural protein (SEQ ID NO:1) and a back-translation computer program (University of Wisconsin, Genetic Computer Group, Sequence Analysis Software Package, Version 5.2). The total gene, 229 base pairs, was synthesized as 14 different oligomers which, when ligated together, form the restriction sequences shown in FIG. 1. As illustrated in FIG. 2, the 14 oligomers were synthesized as 7 essentially complementary pairs of oligonucleotides. The protruding sequences at joining sites of complementary pairs of oligomers were 6 bases in length. The 14 oligomers were assembled in the cloning vector pNN03, a derivative of the commercially available plasmid pUC8. It was created by cleaving out the entire polylinker region of pUC8 by digestion with HindIII and EcoRI. An alternate polylinker containing different restriction sites (FIG. 3) was synthesized by standard procedures and ligated in the HindIII/EcoRI-cleaved pUC8. A restriction map of pNN03 is depicted in FIG. 4.

Plasmid pNN03 was cleaved with restriction enzymes NcoI and HindIII. The 14 oligomers were added to the cleaved vector and ligation was achieved with T4 ligase. E. coli cells were then transfected with the ligated mixture and colonies expressing tetracycline resistance were isolated. Plasmids were isolated from these colonies and examined by restriction mapping and nucleotide sequencing to determine if they contain the intact synthetic applaggin gene. One of the plasmids demonstrating the integrity of an assembled vector, termed pNN03-applaggin, was used to construct the appilog genes of this invention.

To construct the Met-N-appilog gene, we digested 21.6 ng of pNN03-applaggin with 50 units of BsmI at 60° C. for 2 hours. We then adjusted the NaCl concentration up to 150 mM, added 50 units of NcoI and continued digestion at 37° C. for an additional 2 hours. The digestion mixture was electrophoresed on a 0.7% agarose gel run at 100 volts for approximately 1 hour and visualized with ethidium bromide. We excised the large fragment from the gel and electroeluted the DNA. Electroelution was performed at 100 volts for 1 hour.

We synthesized the portion of the gene coding for the thrombin inhibitory domain of Met-N-appilog as 3 pairs of complementary oligonucleotides containing 5' and 3' overhangs for complementary assembly (FIG. 5). Additionally, oligonucleotide 1 contained an overhang that complemented the NcoI end of the fragment from pNN03-applaggin (CATG), while oligonucleotide 5 contained an overhang that complemented the BsmI end of the pNN03-applaggin fragment (5'-CG-3'). After synthesis, the oligonucleotides were treated with T4 kinase in the presence of ATP to add a phosphate group onto the 5' ends. We then heated all six oligonucleotides together to 90° C. and allowed the solution to slowly cool to room temperature in order to anneal the complementary strands and the complementary overhangs. We then assembled the Met-N-appilog gene by ligating the annealed oligonucleotides (3.3 pmoles) together with approximately 200 ng of the large BsmI/NcoI fragment from pNN03-applaggin.

To construct the Met-C-appilog gene, 21.8 ng of pNN03-applaggin was digested with 40 units of PstI. We then adjusted the NaCl concentration up to 50 mM, added 40 units of HindIII and continued digestion at 37° C. for an additional 2 hours. We electrophoresed the digestion mixture on a 0.7% agarose gel and visualized the bands with ethidium bromide. The large fragment was then excised and electroeluted. We synthesized the portion of the gene coding for the thrombin inhibitory domain of Met-C-appilog as 3 pairs of complementary oligonucleotides containing 5' and 3' overhangs for complementary assembly (FIG. 6). Additionally, oligonucleotide 2 contained an overhang that complemented the PstI end of the fragment from pNN03-applaggin (ACGT), while oligonucleotide 6 contained an overhang that complemented the HindIII end of the pNN03-applaggin fragment (TCGA). The oligonucleotides were kinased and annealed as described previously. The Met-C-appilog gene was assembled by ligating 3.3 pmoles of the annealed oligonucleotides together with 200 ng the large PstI/HindIII fragment from pNN03-applaggin.

The Met-N- and Met-C-appilog ligation products were then used to separately transform E. coli JA221 cells which were then plated on LB agar+ampicillin (100 μg/ml) plates. Plasmids from several colonies were isolated and analyzed by restriction enzyme analysis and DNA sequencing. We used plasmid pNN0-C-appilog #7 and pNN0-N-appilog #7 for further manipulations.

EXAMPLE 2

Construction Of OmpA-Appilog Expression Vectors

The plasmid vector pIN-III-ompA[1], which has been previously described [J. Ghrayeb et al., "Secretion Cloning Vectors in *Escherichia coli*", *EMBO J.*, 3, pp. 2437-42 (1984)], allows fusion of protein coding sequences to the signal sequence of outer membrane protein A (OmpA). The ompA signal sequence is capable of directing export of proteins across the bacterial inner membrane into the periplasm.

Initially, we digested approximately 10 μg each of plasmid pNNO-C-appilog #7 and pNNO-N-appilog #7 with 20 units of NcoI. The digestion product was purified by phenol/chloroform extraction, followed by Na acetate/ethanol precipitation. The digestion product was then blunt-ended to remove the resulting overhangs by digestion with 10 units Mung Bean Nuclease [Pharmacia-LKB, Piscataway, N.J.] for 10 minutes at 37° C. in 30 mM Na acetate, 50 mM NaCl, 1 mM ZnCl, pH 4.6. Following digestion, we added EDTA to a final concentration of 10 mM. The DNA was then extracted with phenol/chloroform and Na acetate/ethanol precipitated. Each of the vectors was then cleaved with 100 units of HindIII. The 300 bp fragment of Met-C-appilog or Met-N-appilog was then purified by agarose gel electrophoresis on a 1% gel, followed by excision of the band and electroelution of the DNA into dialysis bags at 50 volts for 30 minutes. The DNA was then concentrated by ethanol precipitation.

We digested 10 μg of vector pIN-III-ompA[1] with 20 units of EcoRI. The digestion product was blunt-ended with Mung Bean nuclease as previously described. We then cleaved the vector with 100 units of HindIII to release a 7.5 kb fragment. We electrophoresed the digestion mixture on a 1% agarose gel and excised the 7.5 kb fragment. The DNA was electroeluted into a dialysis bag and purified by ethanol precipitation.

We then ligated 40 ng of the 300 bp appilog DNA fragment (from Met-C- or Met-N-appilog) to 200 ng of the 7.5 kb pIN-III-ompA vector fragment with T4 ligase. We then transformed E. coli strain JA221[lacIg] with the ligation mixture and plated transformants on LB agar+ampicillin (100 μg/ml). Colonies were screened for the presence of the desired plasmid by colony hybridization with the [32]p-labeled, 400 base pair NcoI-PvuII fragment of pNNO-N-appilog #7, which contained the N-appilog gene. Positive colonies were picked and grown overnight in 5 ml of LB broth+ampicillin (100 μg/ml). We took 0.1 ml of the overnight culture and inoculated into 5 ml of fresh media. The cultures were grown for 4 hours at 37° C. We then added 1 mM IPTG to the cultures to induce appilog expression and continued incubation for 2 hours. We centrifuged 1 ml of the induced culture and resuspended the cell pellet in 100 μl of SDS-PAGE loading buffer. The sample was boiled for 5 minutes and loaded onto a 16% polyacrylamide-SDS gel. After running the gel, the proteins were transferred to nitrocellulose paper and screened for the expression of appilog protein by Western Blot analysis using rabbit anti-applaggin antibodies. No colonies expressed any polypeptides which reacted positively in the Western Blot. DNA sequence analysis of one of the clones containing the Met-C-appilog gene, pIN-III-ompA1-CAPLG-B5, revealed that the expected junction between the ompA signal sequence and the appilog coding sequences was incorrect and therefore the C-appilog sequence was not in frame with the ompA signal sequence.

Figure 7:
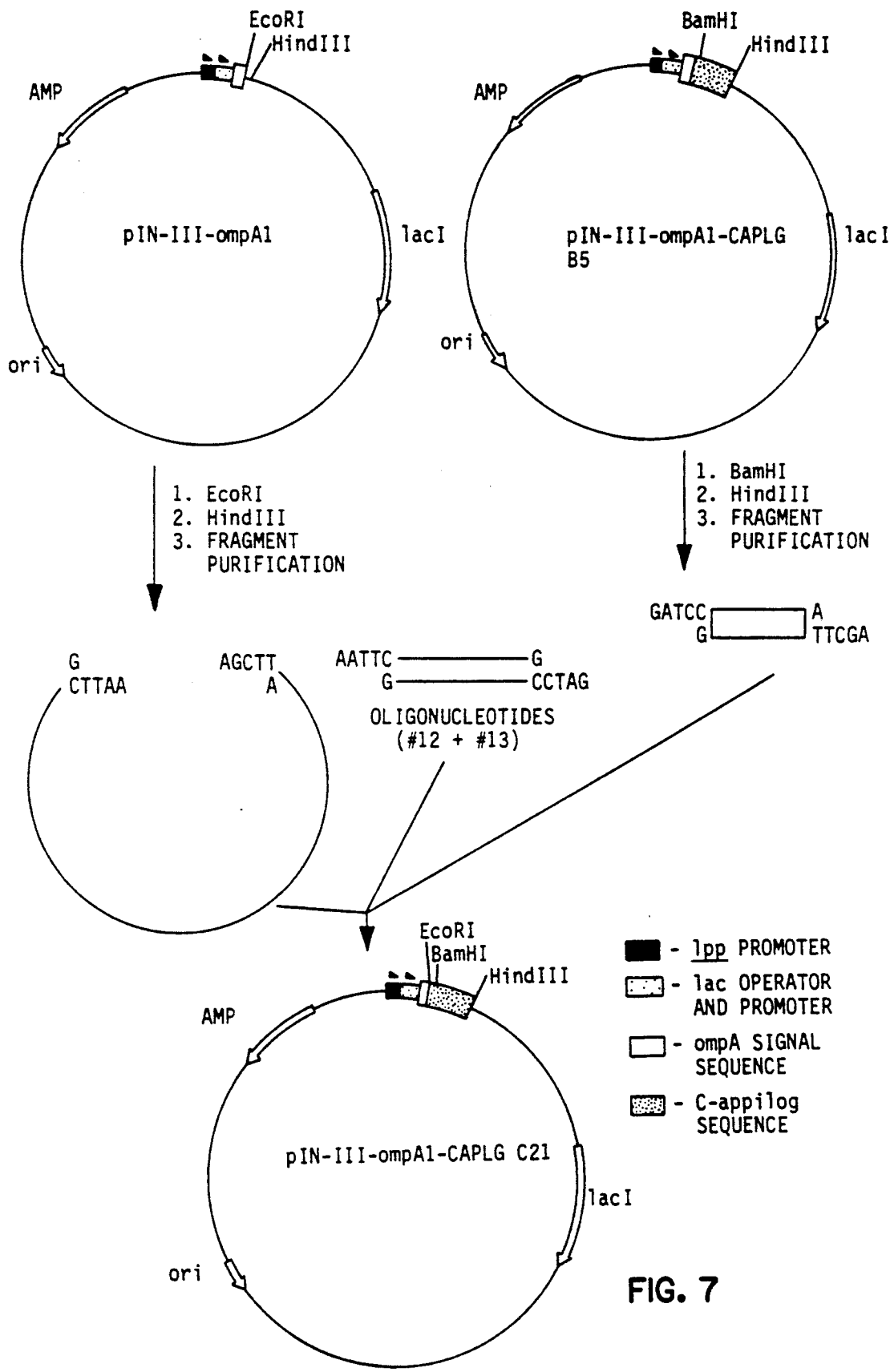
FIG. 7 depicts, in schematic form, the construction of a vector capable of directing the expression of an ompA-C-appilog fusion polypeptide.

We therefore attempted a second strategy for cloning the appilog gene into pIN-III-ompA1. This scheme is depicted in FIG. 7. We cleaved pIN-III-ompA1 with EcoRI and HindIII as described above and purified the large, 7.5 kilobase (kb) fragment by agarose gel electrophoresis on a 1% gel, followed by excision of the fragment, electroelution and ethanol precipitation. We next cleaved 10 μg of pIN-III-ompA1-CAPLG-B5 simultaneously with 24 units of BamHI and 20 units HindIII to release a 270 bp fragment containing all of the Met-C-appilog gene except for approximately the first 30 nucleotides (the BamHI site spans the codons for Gly-Ser at amino acids 9 and 10). The resulting fragment was gel purified and electroeluted as previously described. We then synthesized a pair of partially complementary oligonucleotides which, when inserted between the EcoRI site of the pIN-III-ompA1 fragment and the BamHI site of the C-appilog gene, built back the missing portion of the C-appilog coding region and kept the appilog gene in frame with the ompA signal sequence. These oligonucleotides had the sequence (SEQ ID NO:12): 5'-AATTCGGAAGCTGGTGAAGAATG-CGACTGCG-3'; and (SEQ ID NO:13): 5'-GATCC-GCAGTCGCATTCTTCACCAGCTTCCG-3'. The resulting gene coded for an ompA signal sequence-Ala-Asn-Ser-C-appilog fusion protein.

We boiled the 20 pmoles of each of the above oligonucleotides for 2 minutes and allowed the solution to slowly cool to room temperature to effect annealing. We then ligated together 200 ng of the 7.5 kb fragment from pIN-III-ompA1, 40 ng of the 270 bp BamHI-HindIII fragment of pIN-III-ompA1-CAPLG-B5 and 5 pmoles of the annealed oligonucleotides with T4 ligase and used the ligation mixture to transform JA221[lacIg] cells. Transformants were grown on LB agar+ampicillin (100 μg/ml). Plasmid DNA from random colonies was prepared and analyzed by digestion with EcoRI to show that the desired junction between the ompA signal sequence and the synthetic oligonucleotides was generated. Clones containing the correct construction are linearized by digestion with EcoRI. DNA sequencing of one positive plasmid, pCAPLG-C21, confirmed the presence of the correct sequence. This construct coded for the ompA signal sequence, followed by Ala-Asn-Ser-C-appilog.

Figure 8:
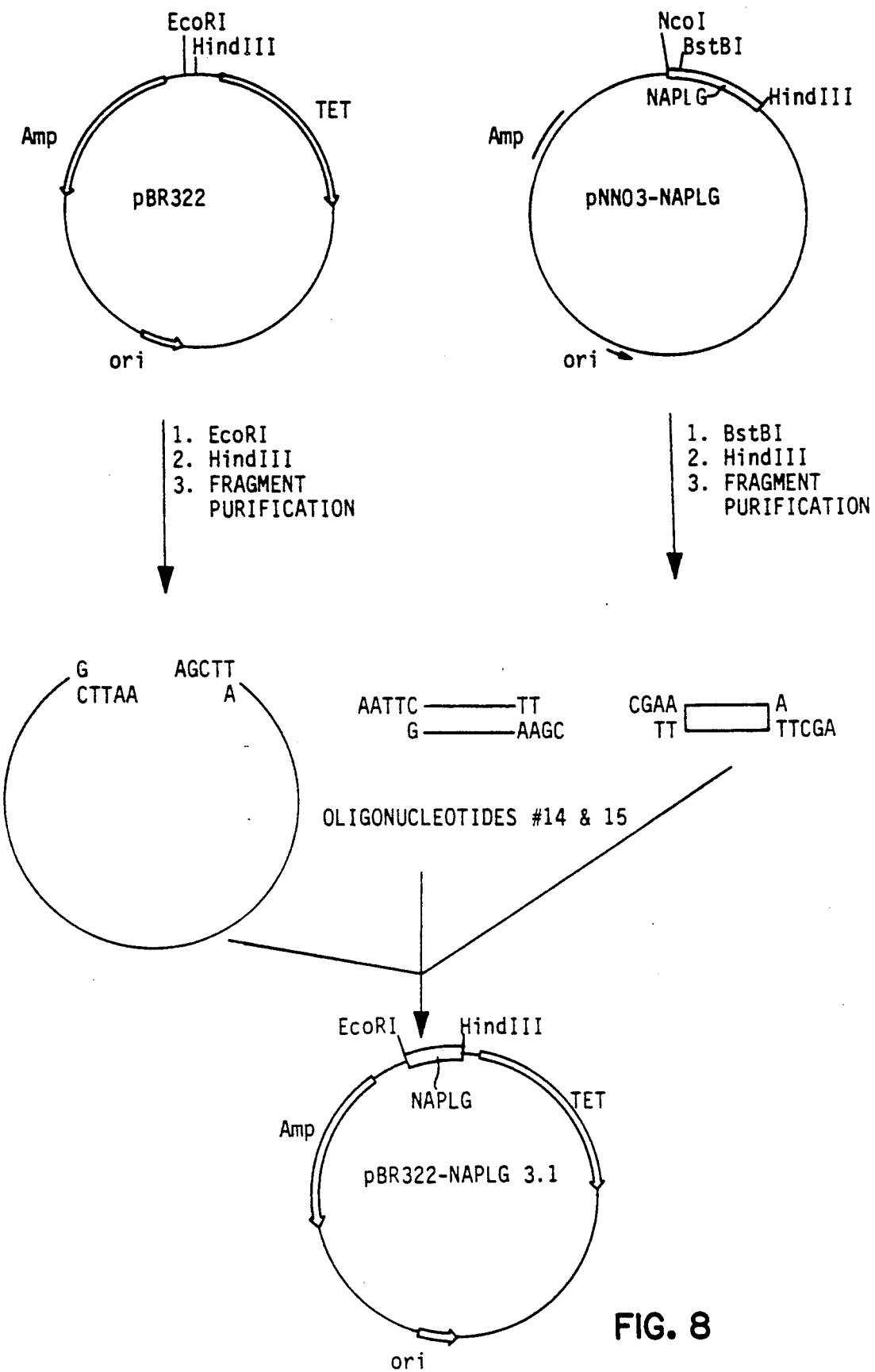
FIG. 8 depicts, in schematic form, the construction of a vector capable of directing the expression of an ompA-N-appilog fusion polypeptide.
Figure 8:
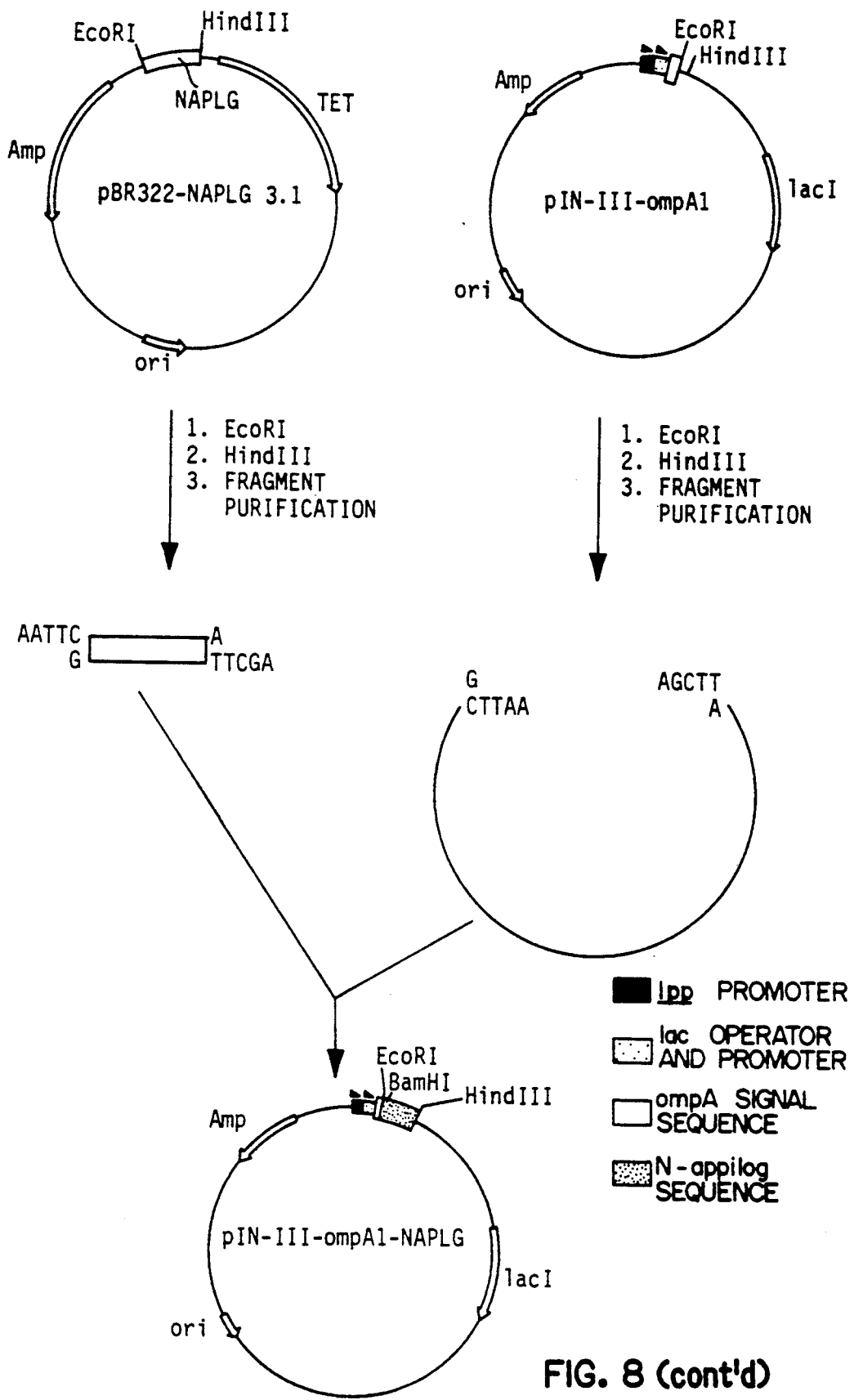

An alternate strategy for the cloning of the N-appilog gene into pIN-III-ompA1 is depicted in FIG. 8. Specifically, we digested 10 μg of pBR322 simultaneously with 20 units of EcoRI and 20 units HindIII. We then purified the large 4,322 bp fragment by gel electrophoresis on a 1% agarose gel, excision of the band, electroelution of the DNA and ethanol precipitation. The plasmid pNN0-N-appilog #7 (10 μg) was cleaved with 40 units of BstBI at 65° C. for 2 hours under mineral oil. We then added 20 units of HindIII to the digestion mixture and incubated at 37° C. for an additional 2 hours. This digestion released a 249 bp fragment containing the C-terminal coding region of N-appilog (BstBI cleaves between the codons for amino acids 11 and 12 of the polypeptide).

We then synthesized a pair of partially complementary oligonucleotides which could be inserted between the EcoRI end of pBR322 and the BstBI end of the N-appilog gene and would regenerate the first 12 amino acids of N-appilog. The oligonucleotides had the nucleotide sequences (SEQ ID NO:14):

5'-
    AATTCGGGTCCGCGTCCGGGTGGTGGT-
    GGTAACGGTGACTT-3'; and (SEQ ID
    NO:15):

5'-CGAAGTCACCGTTACCACCACCACCC-
    GGACGCGGACCCG-3'.

The resulting gene coded for an ompA signal sequence-Ala-Asn-Ser-N-appilog fusion protein.

We annealed 20 pmoles of each oligonucleotide as previously described. We then ligated together 200 ng of the pBR322 fragment, 40 ng of the N-appilog gene fragment and 5 pmoles of the annealed oligonucleotides with T4 ligase and transformed E. coli strain DH5-alpha with the ligation mixture. Transformants were plated on LB agar+ampicillin (100 μg/ml). Individual colonies were picked and plasmids purified therefrom by the alkaline miniprep technique. The plasmids from random transformants were analyzed by EcoRI/HindIII digestion to identify those releasing an approximately 305 bp fragment. DNA sequencing of one of these positive plasmids, pBR322-NAPLG-3.1, confirmed the presence of the correct coding sequence for Ala-Asn-Ser-N-appilog.

We next grew up a large culture (1 liter) of pBR322-NAPLG-3.1 in LB+ampicillin and prepared plasmid therefrom by the alkaline lysis technique. The resulting plasmid preparation was further purified by CsCl gradient centrifugation. We digested 10 μg of the resulting plasmid with 20 units each of EcoRI/HindIII and isolated the 305 base pair fragment by agarose gel electrophoresis and electroelution. We then ligated the 40 ng of the fragment to 200 ng of the large EcoRI/HindIII fragment of pIN-III-ompA1.

EXAMPLE 3

Expression And Purification Of OmpA-Appilog Expression Products

A fresh colony of pCAPLG-C21 was picked and grown overnight at 37° C. in 10 ml of M-9 media supplemented with 4 mg/ml glucose, 50 μg/ml each of tryptophan, leucine and ampicillin, 2 μg/ml thiamine and 2 mg/ml casamino acids. We then inoculated the overnight culture into 1 liter of the same supplemented M-9 media and grew the culture at 37° C. on a shaker until the cells reached a density of 0.4 OD$_{550}$. We then added 2 mM IPTG to the culture to induce the cells and continued growth for an additional 3 hours.

The cells were then harvested by centrifugation at 4,000×g and the cell pellets were resuspended in 20 ml of cold 20 mM Tris, 1 mM EDTA containing 10 mg PMSF. The suspension was passed twice through a French Press at 1,000 PSI. The soluble cell extract was collected by centrifuging the suspension at 10,000 rpm in an SS34 rotor (Sorval) for 30 minutes at 4° C. The supernatant was precipitated with 40% ammonium sulfate at 4° C. overnight. The ammonium sulfate pellet was isolated by centrifugation and redissolved in 15 ml of 20 mM Tris-HCl, 1 mM EDTA, pH 7.5. We then chromatographed this solution over a G-50 column (2.75×100 cm) at 4° C. in the same buffer. Fractions (7 ml) were collected and aliquots (10 μl) were assayed by Western Blot analysis using rabbit anti-applaggin antibodies (1:1,000 dilution). C-appilog-containing fractions were pooled and further purified by reverse phase HPLC on a C8 column (0.25×10 cm). The column was eluted with a linear gradient of 0 to 50% solution B (70% acetonitrile in 0.085% TFA) over 45 minutes at a flow rate of 1 ml/min.

Fractions were monitored by (absorbance at 214 and 280 nm). C-appilog containing fractions were pooled and subjected to partial amino acid sequence analysis. The 15 N-terminal amino acids were determined to be Ala-Asn-Ser-Glu-Ala-Gly-Glu-Glu-?-Asp-?-Gly-Ser-Pro-Glu, confirming proper construction. The presence of Ala-Asn-Ser at the N-terminus of this C-appilog was expected based on the oligonucleotide linkers used in vector construction.

EXAMPLE 4

Construction Of MalE-Appilog Expression Vectors

Figure 9:
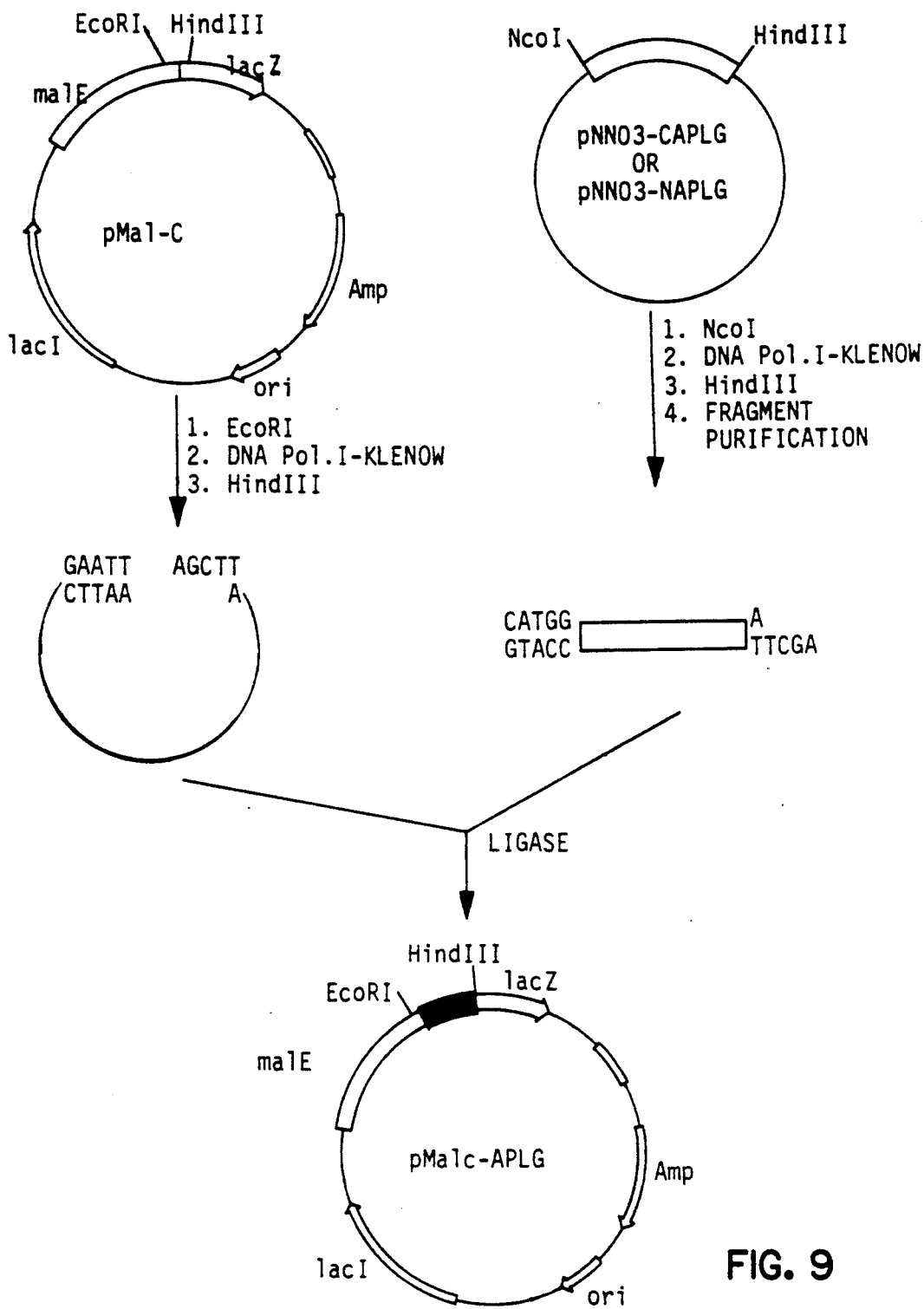
FIG. 9 depicts, in schematic form, the construction of a vector capable of directing the expression of a malE-appilog fusion polypeptide.

Vectors comprising a Met-C-appilog or Met-N-appilog fused to the 3' end of the malE gene were constructed in both the pMAL-c (a vector containing the malE gene without its native signal sequence) and pMAL-p (a vector containing the malE gene together with the native signal sequence) plasmids as depicted in FIG. 9 (New England Biolabs).

Specifically, 10 μg of either pNNO-C-appilog #7 or pNNO-N-appilog #7 (as described in Example 1) were digested with 20 units of NcoI, phenol/chloroform extracted and ethanol precipitated. We then filled in the resulting 5' overhang with 5 units of the Klenow fragment of DNA polymerase I and a mixture of dinucleotidetriphos-phates (dNTPs) for 30 minutes at 25° C. The plasmid was then digested with 20 units of HindIII to release a 300 bp fragment containing the appilog gene. The NcoI-HindIII fragment was isolated by agarose gel electrophoresis, electroelution, and ethanol precipitation.

We digested either pMAL-c or pMAL-p with 20 units of EcoRI. We then extracted, precipitated and treated the digestion product with Klenow fragment, as described above. We next digested the blunt-ended DNA with 20 units of HindIII. The large fragment was isolated from an agarose gel, electroeluted and ethanol precipitated. The purified NcoI-HindIII fragment of either pNN0-C-appilog or pNN0-N-appilog (40 ng) was mixed with the 200 ng of the EcoRI-HindIII fragment from pMAL-c or pMAL-p (4 different constructions in total) and ligated with T4 ligase. We transformed E. coli DH5-alpha cells with the ligated DNA and grew the transformants on LB agar+ampicillin (100 μg/ml)+XG (5-Bromo-4-Chloro-3-Indolyl-galactopyranoside, 40 μg/ml.

We purified 6 white colonies from each ligation and isolated plasmid DNA from each by the alkaline miniprep procedure. We digested each of the plasmids with NcoI and HindIII and ran the digestion mixtures on an agarose gel. Those plasmids releasing an approximately 500 bp fragment were assumed to contain appilog gene inserts. In this manner plasmids pMAL-c-CAPLG (C-appilog insert), pMAL-p-CAPLG, pMAL-c-NAPLG (N-appilog insert), and pMAL-p-NAPLG were isolated. From each construction, at least 5 out of 6 analyzed plasmids contained the expected appilog gene insert. The expected DNA and protein sequence at the MalE-appilog junction is shown in FIG. 10.

EXAMPLE 5

Expression And Detection Of MalE-appilog Fusion Proteins

Two transformants from each construction (i.e., containing plasmids pMAL-c-CAPLG pMAL-p-CAPLG, pMAL-c-NAPLG or pMAL-p-NAPLG) were separately grown in LB medium+ampicillin (100 μg/ml) at 37° C. overnight. We then diluted 0.1 ml of the overnight culture into the 5 ml of the same medium supplemented with 1 mM IPTG and incubated at 37° C. for 4 hrs. We isolated cells from 1 ml of culture by centrifugation, resuspended them in 100 μl of SDS-PAGE loading buffer, and boiled for 3 minutes. We loaded 5 μl of this sample onto a 10% SDS-polyacrylamide gel for electrophoresis. Protein gels were either stained with Coomassie Blue or electroblotted to nitrocellulose and probed with antibody to applaggin in a standard Western Blot immunodetection assay. The positive protein bands were visualized using anti-rabbit IgG conjugated to horseradish peroxidase or alkaline phosphatase and the appropriate colorimetric reagent. All of the assayed transformants produced a detectable protein by Western Blot, confirming that each construction directed the expression of an appilog polypeptide.

EXAMPLE 6

Purification Of MalE-Appilog Fusion Proteins And Isolation Of Appilog By Factor Xa Digestion One of the positive pMAL-c-CAPLG clones was used for larger scale purification of the appilog-containing polypeptide. We grew an overnight culture of this clone in LB media+ampicillin (100 μg/ml). We inoculated 1 liter of LB+ampicillin (50 μg/ml) with 10 ml of the overnight culture and grew the large culture at 37° C. until they reached an OD$_{550}$ of 0.4. We then induced appilog expression by adding IPTG to the culture to a final concentration of 0.3 mM and reincubating at 37° C. for 2 hours. The cells were then harvested by centrifugation at 4,000×g for 20 minutes. The cell pellet was resuspended in 50 ml of lysis buffer (10 mM sodium phosphate, 30 mM NaCl, 0.25% Tween-20, 10 mM β-mercaptoethanol, 10 mM EDTA, 10 mM EGTA, pH 7.0) and the cells then broken open by 2 passages through a French Press at 2,000 psi. We next added NaCl to the solution to a final concentration of 0.5 M and then centrifuged at 9,000×g for 30 minutes. The resulting crude extract was diluted 1:5 with column buffer (10 mM sodium phosphate, 500 mM NaCl, 10 mM β-mercaptoethanol, 1 mM Na azide, 10 mM EGTA, pH 7.0)+0.25% Tween-20 for loading onto an a amylose resin column.

The diluted extract was applied to a 40 ml amylose resin (New England Biolabs) column at a flow rate of 1 ml/min. After loading the sample, the column was washed with 3 column volumes of column buffer containing 0.25% Tween-20 and 5 column volumes of column buffer without Tween-20. The maltose binding protein-containing appilog polypeptide was eluted with column buffer containing 10 mM maltose. Elution was monitored by absorbance at 280 nm. The polypeptide eluted soon after the void volume of the column.

The appilog-containing fractions were pooled and dialyzed overnight against 4 changes of 100 volumes each of 10 mM Tris-HCl, 100 mM NaCl, 2 mM $CaCl_2$, pH 8. Following dialysis, we adjusted the protein concentration to 1 mg/ml and added 20 units of Factor Xa [New England Biolabs]. Digestion was allowed to proceed overnight at room temperature.

After Factor Xa cleavage, the digestion products were purified by HPLC on a C8 reverse phase column (4.6×10 cm). The column was developed with a linear gradient of increasing acetonitrile (0–60%) in 0.1% TFA over 54 minutes at a flow rate of 1 ml/minute. The appilog polypeptide eluted at 23% acetonitrile concentration, prior to the MBP polypeptide. Automated Edman degradation of the purified appilog polypeptide revealed an N-terminal sequence of Gly-Ser-Ile-Glu-Gly-Arg-Pro-Glu-Phe-Met, indicating that Factor Xa had cleaved at an Arg-Gly bond in the fusion protein. The resulting appilog polypeptide was referred to as Gly-Ser-Ile-Glu-Gly-Arg-Pro-Glu-Phe-Met-C-appilog. The cytoplasmic malE-N-appilog fusion protein is similarly purified and has an identical N-terminal amino acid sequence.

A similar series of steps is used to purify and cleave the fusion protein produced from the pMAL-p-appilog constructs. The only difference being that the expressed fusion protein is initially obtained by osmotic shock of the transformed E. coli, instead of cell lysis.

EXAMPLE 7

Other Appilog Constructs

The malE-appilog constructs described in Example 4 can be modified to allow Factor Xa cleavage at a site nearer to the amino terminus of C- or N-appilog and to allow the resulting appilog to have a shorter N-terminal extension. This is achieved by changing the Ile-Glu-Gly-Arg-Pro-Glu-Phe-Met sequence to Ile-Glu-Gly-Arg-Ile-Met. The first four amino acids of the latter sequence is the native Factor Xa cleavage site present in bovine prothrombin [K. Nagai et al., Nature, 309, pp. 810–12 (1984)]. Factor Xa cleaves this sequence in between the Arg and Ile residue, producing an Ile-Met-appilog. Similarly, if the sole methionine residue present within the appilog portion of the malE-appilog fusion protein is changed to another amino acid, cyanogen bromide cleavage of the fusion protein will produce an appilog polypeptide containing no N-terminal extensions.

To effect these changes, a single DNA sequence encoding both of these modified regions is synthesized by the polymerase chain reaction (PCR). This new DNA sequence is then substituted for the corresponding region contained in the original malE-appilog construct.

Figure 11:
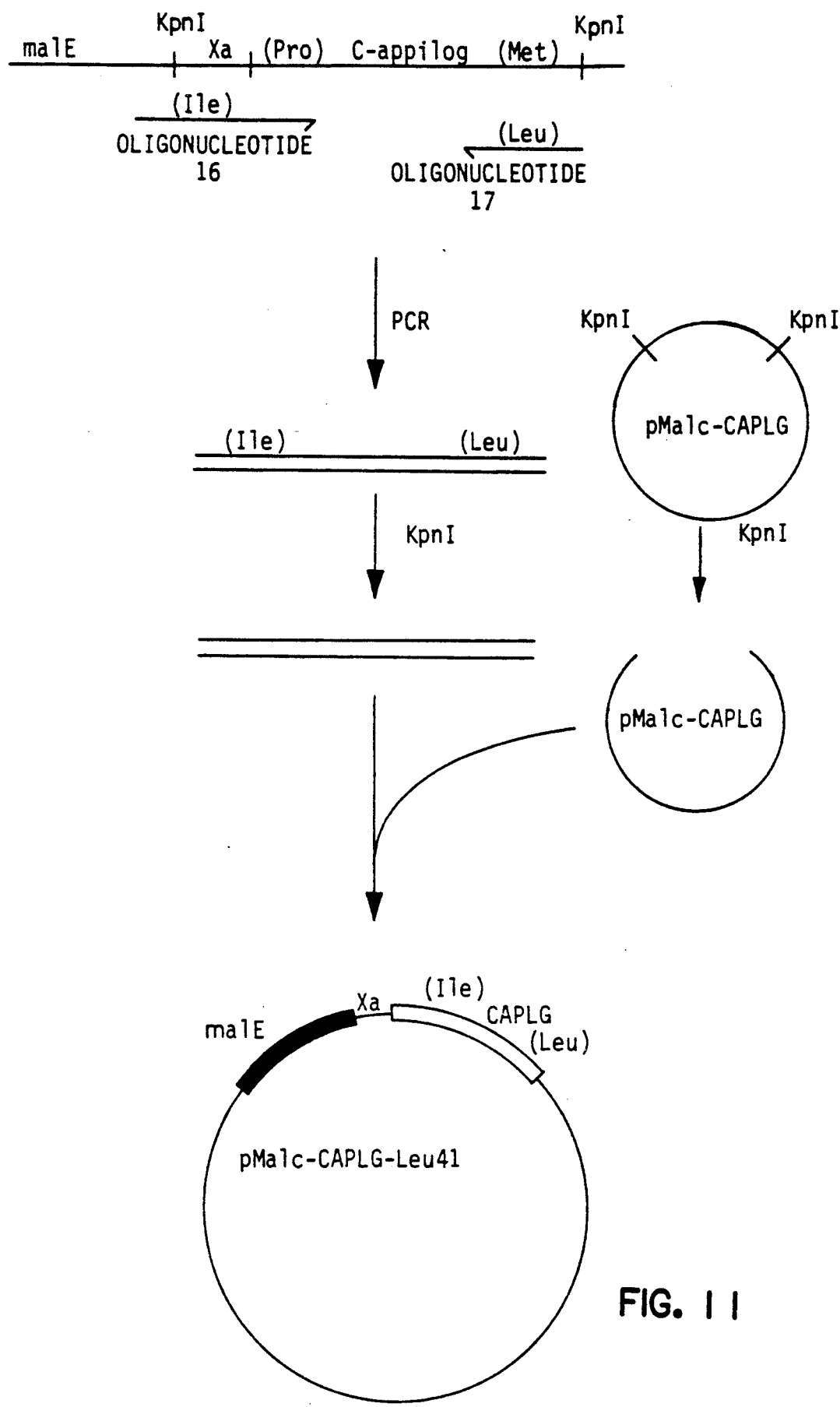
FIG. 11 depicts, in schematic form, an alternate construction of a vector capable of directing expression of a malE-appilog fusion polypeptide.

FIG. 11 depicts the scheme for making these changes in pMAL-c-CAPLG. Specifically, we first synthesize two primers to be used in the PCR procedure. These are (SEQ ID NO:16): 5'-ACGTCGGTAC-CAGGCGCGCGTATCGAGGGTAGGATCATG-GAAGCTGGTGAA-3', which incorporates the Pro-Glu-Phe-Met to Ile-Met change; and (SEQ ID NO:17): 5'-GCAAACGGTACCTTCTTTCAGGAATTT-GCACTGGTC-3', which incorporates the conservative Met to Leu change at amino acid 41 of C-appilog. The primers are then used in PCR amplification techniques employing a Cetus/Perkin-Elmer PCR apparatus and following the manufacturer's directions.

The resulting amplified 180 base pair fragment contains KpnI sites at both ends. Following PCR, the fragment is purified and cleaved with KpnI. Plasmid pMAL-c-CAPLG is also cleaved with KpnI. This removes the fragment corresponding to the PCR synthesized fragment from the vector. The large 6 kb KpnI fragment of pMAL-c-CAPLG is then purified by agarose gel electrophoresis and electroelution. We then ligate the large KpnI fragment of pMAL-c-CAPLG to the KpnI cleaved 180 base pair PCR fragment and use the ligation product to transfect E. coli DH5-alpha cells by the method described in Example 4. Detection of clones containing the proper construct and expressing the desired fusion protein is achieved by the methods described in Example 4 and 5, respectively. Large scale expression, purification and Factor Xa cleavage of the malE-appilog fusion protein is carried out according to the protocol set forth in Example 6. The end product of this procedure is Ile-Met-C-appilog($Leu_{41}$). If the purified fusion protein is treated with cyanogen bromide instead of Factor Xa, the resulting product, which is subsequently purified by reverse phase HPLC, is C-appilog($Leu_{41}$). The same protocol may be used to alter pMAL-p-CAPLG.

A similar series of steps may be carried out with pMAL-c-NAPLG or pMAL-p-NAPLG. When using either of these vectors, the oligonucleotide primer spanning the Factor Xa cleavage site must constructed based on the N-terminal sequence of N-appilog. The internal oligonucleotide will be the same as that used for pMAL-c-CAPLG (SEQ ID NO:17). It will be apparent that the amplified fragment will be approximately 72 bases longer, because the location of the methionine residue in N-appilog is at amino acid 65. The end product of Factor Xa digestion in these constructs is termed Ile-Met-N-appilog($Leu_{65}$). The cyanogen bromide cleaved expression product of these constructs is termed N-appilog($Leu_{65}$).

EXAMPLE 8

Anticoagulant Activity Of Gly-Ser-Ile-Glu-Gly-Arg-Pro-Glu-Phe-Met-C-Appilog

We compared the anticoagulant activities of L-Phe-Hirulog-8 (SEQ ID NO:18; Phe-Pro-Arg-Pro-Gly-Gly-Gly-Gly-Asn-Gly-Asp-Phe-Glu-Glu-Ile-Pro-Glu-Glu-Tyr-Leu, a peptide equivalent to the thrombin inhibitory domain of the bifunctional inhibitors of this invention), applaggin, an equimolar combination of L-Phe-Hirulog-8 and applaggin, and Gly-Ser-Ile-Glu-Gly-Arg-Pro-Glu-Phe-Met-C-appilog using pooled, normal human plasma (George King Biomedical, Overland Park, Kans.) and a Coag-A-Mate XC instrument (General Diagnostics, Organon Technica, Oklahoma City, Okla.). Activity was monitored using the activated partial thromboplastin time (APTT) assay with $CaCl_2$ and phospholipid solutions obtained from the manufacturer. The various inhibitors were then added to separate APTT determination wells at final concentrations of 0 to 10 μM in a total volume of 25 μl prior to addition of 100 μl of plasma.

Figure 12:
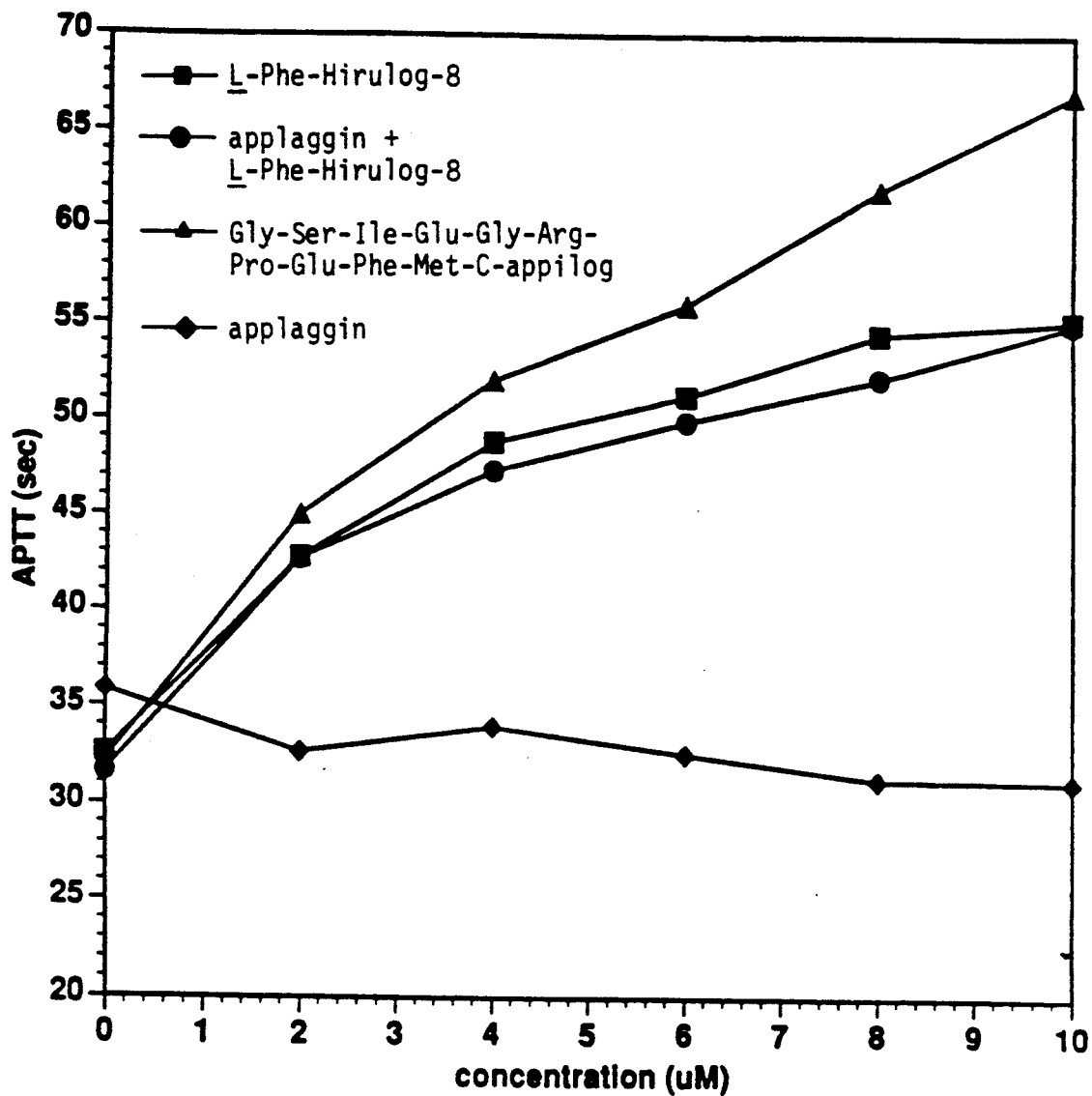
FIG. 12 depicts the comparative effects of L-Phe-Hirulog-8, applaggin, a combination of L-Phe-Hirulog-8 and applaggin, and Gly-Ser-Ile-Glu-Gly-Arg-Pro-Glu-Phe-Met-C-appilog on the APTT of normal human plasma.

The control APTT (absence of inhibitor) was 32 seconds. FIG. 12 shows the results of these dose-dependency studies. This study showed that APTT was increased by Gly-Ser-Ile-Glu-Gly-Arg-Pro-Glu-Phe-Met-C-appilog in a dosedependent manner. FIG. 12 also shows that Gly-Ser-Ile-Glu-Gly-Arg-Pro-Glu-Phe-Met-C-appilog increased APTT by a greater amount that any of the other 2 inhibitors, either alone or in combination. Other appilogs of this invention may be assayed in a similar manner and will show a similar dose-dependent increase in APTT.

EXAMPLE 9

Inhibition Of Platelet Aggregation And Release

We prepared platelet-rich plasma from healthy human volunteers for use in various platelet assays. More specifically, blood was collected via a 21 gauge butterfly cannula, using a two-syringe technique, into 1/10 volume of 3.8% trisodium citrate. Platelet-rich plasma was prepared by room temperature centrifugation of the citrated whole blood for 15 minutes at 100×g. The platelet rich plasma contained approximately 357,000 platelets/μl. We prepared platelet-poor plasma by centrifuging the citrated whole blood for 2 minutes at 12,000×g.

Figure 13:
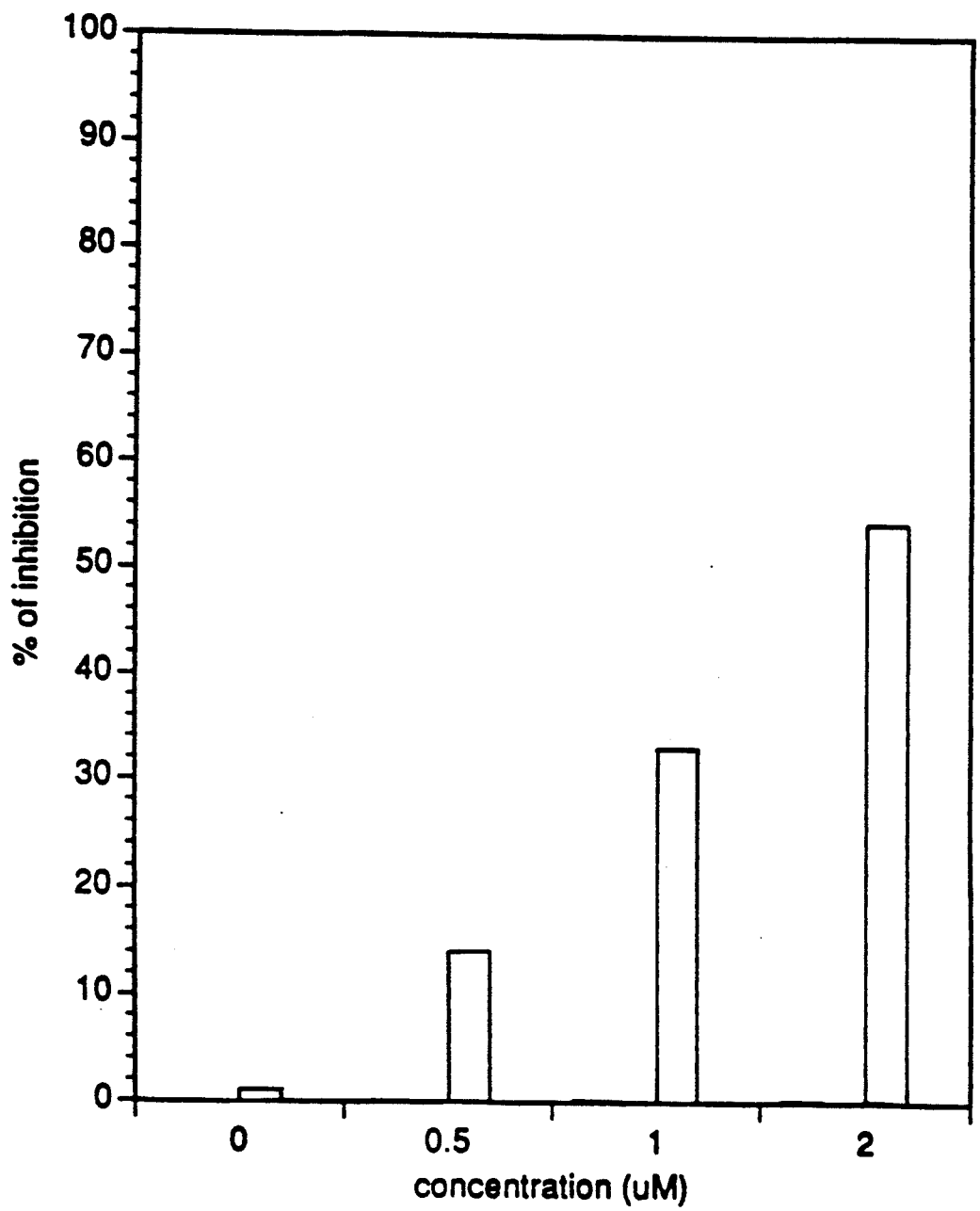
FIG. 13 depicts the effect of Gly-Ser-Ile-Glu-Gly-Arg-Pro-Glu-Phe-Met-C-appilog on collagen-induced platelet aggregation.

Platelet aggregation was assayed in a 4-channel platelet aggregation profiler (PAP4, Biodata, Hatboro, Penna.) according to the manufacturer's directions. We studied inhibition of platelet aggregation effected by Gly-Ser-Ile-Glu-Gly-Arg-Pro-Glu-Phe-Met-C-appilog by adding varying amounts (0–2 μM, final concentration) of the polypeptide to stirred human platelet-rich plasma. Specifically, we incubated the appilog with the 0.45 ml of platelets for 1 minute at 37° C. prior to the addition of collagen (60 μg/ml) FIG. 13 demonstrates that Gly-Ser-Ile-Glu-Gly-Arg-Pro-Glu-Phe-Met-C-appilog inhibited platelet aggregation induced by collagen in a dose-dependent manner.

Figure 14:
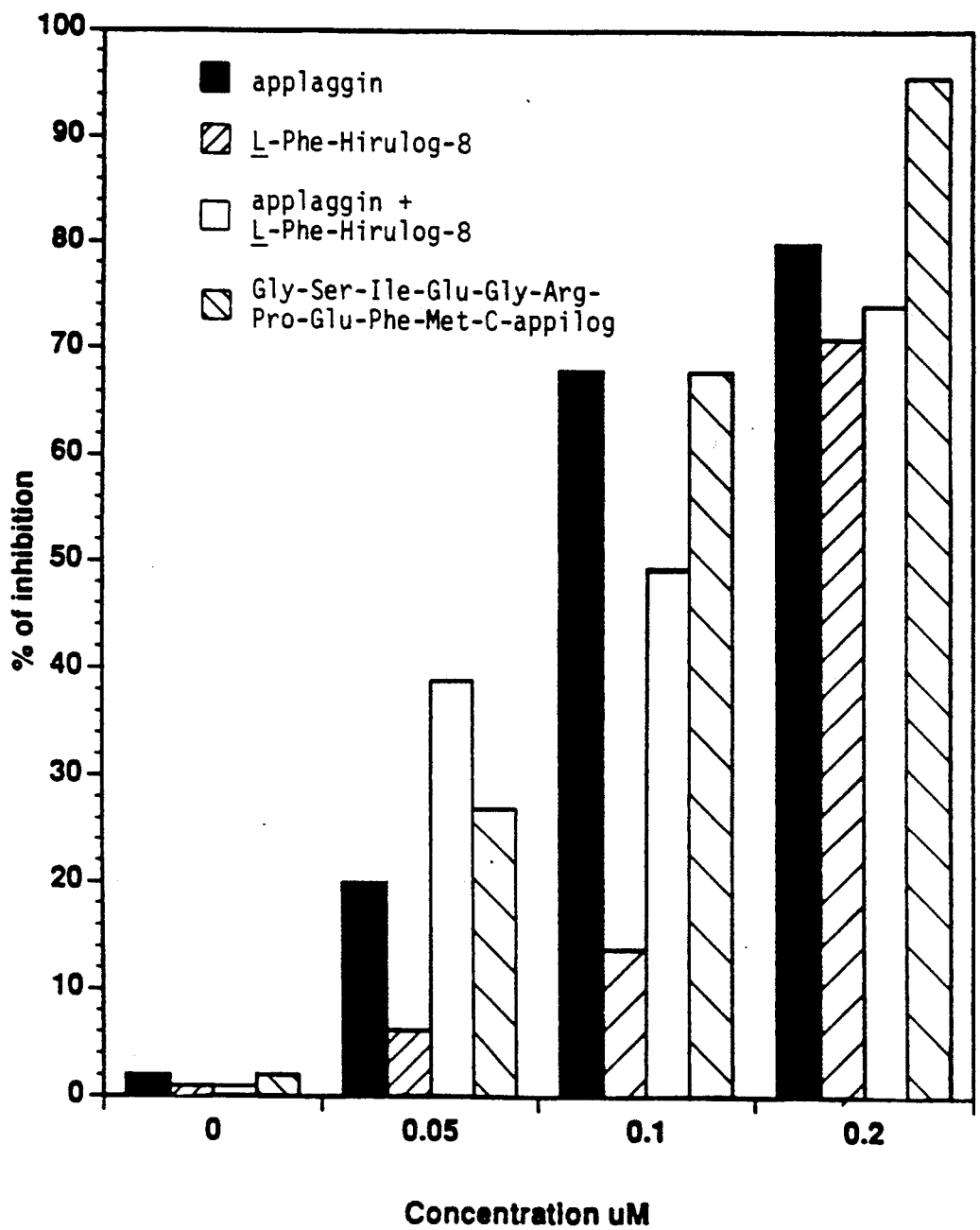
FIG. 14 depicts the comparative effects of L-Phe-Hirulog-8, applaggin, a combination of L-Phe-Hirulog-8, and applaggin, and Gly-Ser-Ile-Glu-Gly-Arg-Pro-Glu-Phe-Met-C-appilog on thrombin-induced platelet aggregation.

To assay the effect of this appilog on the inhibition of thrombin-induced platelet aggregation, we first gel filtered the above platelet preparation using procedures described by B. Chao et al., Proc. Natl. Acad. Sci. USA, 86, pp. 8050–54 (1989). We performed the assay as above, using appilog in a range of 0–0.2 μM in the presence of 0.4 units/ml thrombin. We compared the inhibitory effect of this appilog to equimolar concentrations of applaggin; L-Phe-Hirulog-8; and in equimolar combination of applaggin and L-Phe-Hirulog-8. FIG. 14 depicts the result of this dose-dependency study. As with collagen, Gly-Ser-Ile-Glu-Gly-Arg-Pro-Glu-Phe-Met-C-appilog inhibited thrombin-induced platelet aggregation in a dose-dependent manner. Moreover, at 0.1 and 0.2 μM concentrations, appilog demonstrated superior inhibition of platelet aggregation over the combination of applaggin and L-Phe-Hirulog-8. Other appilogs of this invention are similarly assayed for the ability to inhibit platelet aggregation and display similar inhibitory activity.

The ability of appilog to inhibit the release of $^{14}$C-serotonin from platelets is also measured. Platelets in a plasma suspension are loaded with [$^{14}$C]-serotonin (Amersham, Arlington Heights, Ill.) by incubation at 37° C. for 30 minutes. Following this treatment, platelets are gel filtered. Stirred [$^{14}$C]-serotonin loaded platelets in Tyrode-HEPES buffer (0.5 ml) are incubated at 37° C. with varying amounts of appilog, applaggin or L-Phe-Hirulog-8. Platelets are then stimulated by the addition of 0.4 units of thrombin. At varying times after the addition of thrombin (0–30 minutes), the reaction is terminated and serotonin release and reuptake blocked by the addition of a 1/10th volume of ice-cold ETPI cocktail (3.3% EDTA, 10 mM theophylline, 1 μg/ml prostaglandin E1 and 500 μM imipramine). Following the addition of ETPI, platelets are recovered by centrifugation at 12,000×g for 2 minutes. Release is measured by liquid scintillation counting of [$^{14}$C]-radioactivity. At concentrations of 0.5 μM, appilog strongly inhibits serotonin release over the full 30 minute course of the investigation, while applaggin demonstrates no significant effect on the platelet release reaction. At the same molar concentration, L-Phe-Hirulog-8 inhibits serotonin release, but to a lesser extent than the appilog.

EXAMPLE 10

Inhibition Of Metastatic Cell Growth By Appilogs

The anti-metastatic activity of the bifunctional inhibitors of this invention, preferably an appilog, is assayed using sarcoma T241 cells [L. A. Liotta et al., Nature, 284, pp. 67–68 (1980)] and syngeneic C57BL/6 mice (Jackson Laboratory, Bar Harbor, Me.). The mice are injected either intravenously or subcutaneously with 0–250 g/kg of appilog, followed by injection with $10^4$–$10^6$ T241 tumor cells. After 15 days, the animal is sacrificed and lung tumor colonies are quantitated. Anti-metastatic activity of appilog is measured as percent reduction in tumor colonies compared to placebo-treated control mice. Appilogs demonstrate anti-metastatic activity in this assay.

In an alternative assay, aliquots of human melanoma cells (1–5×$10^6$ cells) are treated with varying amounts (0–50 μg/ml) of appilog. The cells are then grafted onto the subcutaneous, ventral surface of nude mice.

The mice which receive appilog-treated cells are given two daily subcutaneous injections of appilog (0.1 mg/kg). Control mice, which are grafted with untreated cells, are given subcutaneous injections of saline twice daily. Tumor growth in both experimental and control mice is monitored over a 30 day period by measurement of the tumor mass. The experimental mice display smaller tumors than the control mice at the end of the 30 day period.

EXAMPLE 11

Effect Of A Combination Of tPA And Appilog On Thrombolysis

A rat model for arterial thrombolysis is used to determine the effect of appilog on potentiating tPA-induced thrombolysis. In this model, an experimental thrombus is formed in the abdominal aorta following balloon catheter denudation and high grade (95%) stenosis. Blood flow and blood pressure are recorded distal to the site of injury and stenosis. Test animals are randomized the to receive tPA (1.0 mg/kg bolus followed by 1.0 mg/kg/hr infusion) together with saline or appilog (0.6 mg/kg bolus followed by 0.02 mg/kg/hr infusion). The appilog or saline is administered concomitant with tPA and for an additional 50 minutes following the end of tPA infusion.

Animals treated with tPA+appilog exhibit significantly lower reperfusion times, greater reocclusion times and greater times of vessel patency than animals treated with tPA+saline. Therefore appilogs may be used to increase the efficacy of tPA. Moreover, compositions comprising appilog together with tPA may advantageously contain tPA at lower than conventional dosages without sacrificing efficacy. The use of such lower quantities of tPA reduces the risk of side effects associated with tPA administration.

While we have hereinbefore presented a number of embodiments of this invention, it is apparent that our basic construction can be altered to provide other embodiments which utilize the molecules, compositions, combinations and methods of this invention. Therefore, it will be appreciated that the scope of this invention is to be defined by the claims appended hereto rather than the specific embodiments which have been presented hereinbefore by way of example.

---

We claim:

1. A DNA sequence coding on expression for a bifunctional inhibitor of platelet activation and thrombin, said DNA sequence comprising the nucleic acid sequence (SEQ ID NO:10): GGT CCG CGT CCG GGT GGT GGT GGT AAC GGT GAC TTC GAA GAA ATC CCG GAA GAA TAC CTG GGT GGT GGT GGT GAA GCT GGT GAA GAA TGC GAC TGC GGA TCC CCG GAA AAC CCG TGC GAC GAC GCT GCT ACC TGC AAA CTG CGT CCG GGT GCT CAG TGC GCT GAA GGT CTG TGC TGC
GAC CAG TGC AAA TTC NNN AAA GAA GGT
ACC GTT TGC CGT CGT GCT CGT GGT GAC
GAC GTT AAC GAC TAC TGC AAC GGT ATC
TCT GCA GGT TGC CCG CGT AAC CCG TTC
CAC, or a nucleic acid sequence degenerate thereto, wherein each N, either the same or different, is any nucleotide, with the proviso that triplet NNN is not TAA, TAG or TGA.

2. A DNA sequence coding on expression for a bifunctional inhibitor of platelet activation and thrombin, said DNA sequence comprising the nucleic acid sequence (SEQ ID NO:11): GAA GCT GGT GAA
GAA TGC GAC TGC GGA TCC CCG GAA AAC
CCG TGC GAC GAC GCT GCT ACC TGC AAA
CTG CGT CCG GGT GCT CAG TGC GCT GAA
GGT CTG TGC TGC GAC CAG TGC AAA TTC
NNN AAA GAA GGT ACC GTT TGC CGT CGT
GCT CGT GGT GAC GAC GTT AAC GAC TAC
TGC AAC GGT ATC TCT GCA GGT TGC CCG
CGT AAC CCG TTC CAC GGT GGT GGT GGT
GGT CCG CGT CCG GGT GGT GGT GGT AAC
GGT GAC TTC GAA GAA ATC CCG GAA GAA
TAC CTG, or a nucleic acid sequence degenerate thereto, wherein each N, either the same or different, is any nucleotide, with the proviso that triplet NNN is not TAA, TAG or TGA.

3. A vector comprising a first DNA sequence selected from the group consisting of:
   a) SEQ ID NO:10, or a nucleic acid sequence degenerate thereto, wherein each N, either the same or different, is any nucleotide, with the proviso that triplet NNN is not TAA, TAG or TGA; and
   b) SEQ ID NO:11, or a nucleic acid sequence degenerate thereto, wherein each N, either the same or different, is any nucleotide, with the proviso that triplet NNN is not TAA, TAG or TGA.

4. The vector according to claim 3, further comprising a second DNA sequence coding for an OmpA signal sequence, said second DNA sequence being operatively linked to said first DNA sequence.

5. The vector according to claim 3, further comprising a second DNA sequence encoding a maltose binding protein, said second DNA sequence being linked to said first DNA sequence so as to code on expression for a fusion protein having the formula:

$$Z_1\text{-}Z_2\text{-}Z_3\text{-}Z_4$$

wherein $Z_1$ is hydrogen or the amino acid sequence of a signal sequence of said maltose binding protein, $Z_2$ is the amino acid sequence of said maltose binding protein, $Z_3$ is a peptide bond or from 1 to 20 residues, either the same or different, of any amino acid, and $Z_4$ is the amino acid sequence of a bifunctional inhibitor comprising the amino acid sequence of SEQ ID NO:2 or SEQ ID NO:3, wherein Xaa is any amino acid.

6. A host cell transformed with a vector according to any of claims 3 to 5, wherein said host cell is selected from the group consisting of bacterial cells, animal cells, yeast and other fungal cells and plant cells.

7. The host cell according to claim 6, wherein said host cell is *Escherichia coli*.

8. A process for producing a bifunctional inhibitor comprising the amino acid sequence of SEQ ID NO:2 or SEQ ID NO:3, wherein Xaa is any amino acid, said process comprising the steps of:
   a) culturing a host cell according to claim 6; and
   b) recovering said bifunctional inhibitor from said culture.

9. A process for producing a bifunctional inhibitor comprising the amino acid sequence of SEQ ID NO:2 or SEQ ID NO:3, wherein Xaa is any amino acid, said process comprising the steps of:
   a) culturing an *E. coli* host cell harboring a vector according to claim 5, wherein $Z_1$ is hydrogen;
   b) isolating said host cell from said culture;
   c) extracting a soluble cytoplasmic fraction from said host cell;
   d) contacting said cytoplasmic fraction with an amylose chromatography resin under a first buffer condition which allows a maltose binding protein-containing molecule to bind to said resin;
   e) transferring said amylose chromatography resin to a second buffer condition which allows said maltose binding protein-containing molecule to elute from said resin;
   f) digesting said eluted maltose binding protein-containing molecule with Factor Xa to separate a maltose binding protein portion of said fusion protein from a bifunctional inhibitor portion of said fusion protein; and
   g) recovering the bifunctional inhibitor portion from said digest.

10. A process for producing a bifunctional inhibitor comprising the amino acid sequence of SEQ ID NO:2 or SEQ ID NO:3, wherein Xaa is any amino acid, said process comprising the steps of;
    a) culturing an *E. coli* host cell harboring a vector according to claim 5, wherein $Z_1$ is said maltose binding protein signal sequence;
    b) isolating said host cell from said culture;
    c) extracting a soluble periplasmic fraction from said host cell;
    d) contacting said periplasmic fraction with an amylose chromatography resin under a first buffer condition which allows a maltose binding protein-containing molecule to bind to said resin;
    e) transferring said amylose chromatography resin to a second buffer condition which allows said maltose binding protein-containing molecule to elute from said resin;
    f) digesting said eluted maltose binding protein-containing molecule with Factor Xa to separate a maltose binding protein portion of said fusion protein from a bifunctional inhibitor portion of said fusion protein; and
    g) recovering the bifunctional inhibitor portion from said digest.

11. A process for producing a bifunctional inhibitor comprising the amino acid sequence of SEQ ID NO:2 or SEQ ID NO:3, wherein Xaa is any amino acid except methionine, said process comprising the steps of:
    a) culturing an *E. coli* host cell harboring a vector according to claim 5, wherein $Z_1$ is hydrogen;
    b) isolating said host cell from said culture;
    c) extracting a soluble cytoplasmic fraction from said host cell;
    d) contacting said cytoplasmic fraction with an amylose chromatography resin under a first buffer condition which allows a maltose binding protein-containing molecule to bind to said resin;
    e) transferring said amylose chromatography resin to a second buffer condition which allows said maltose binding protein-containing molecule to elute from said resin;

f) treating said eluted maltose binding protein-containing molecule with cyanogen bromide to separate a maltose binding protein portion of said fusion protein from a bifunctional inhibitor portion of said fusion protein; and g) recovering the bifunctional inhibitor portion from said digest.

12. A process for producing a bifunctional inhibitor comprising the amino acid sequence of SEQ ID NO:2 or SEQ ID NO:3, wherein Xaa is any amino acid except methionine, said process comprising the steps of:

a) culturing an *E. coli* host cell harboring a vector according to claim 5, wherein $Z_1$ is said maltose binding protein signal sequence;

b) isolating said host cell from said culture;

c) extracting a soluble periplasmic fraction from said host cell;

d) contacting said periplasmic fraction with an amylose chromatography resin under a first buffer condition which allows a maltose binding protein-containing molecule to bind to said resin;

e) transferring said amylose chromatography resin to a second buffer condition which allows said maltose binding protein-containing molecule to elute from said resin;

f) treating said eluted maltose binding protein-containing molecule with cyanogen bromide to separate a maltose binding protein portion of said fusion protein from a bifunctional inhibitor portion of said fusion protein; and g) recovering the bifunctional inhibitor portion from said digest.

* * * * *

UNITED STATES PATENT AND TRADEMARK OFFICE
CERTIFICATE OF CORRECTION

PATENT NO. : 5,242,810

DATED : September 7, 1993

INVENTOR(S) : John M. Maraganore et al.

It is certified that error appears in the above-identified patent and that said Letters Patent is hereby corrected as shown below:

On the title page:
Abstract, line 10, "he" should be -- the --.

Column 5, line 2, "platelets" should be -- platelet --.

Column 6, line 63, after "and", second occurrence,
           insert -- 5- --.

Column 7, line 50, to column 8, line 7, replace the four
           depicted molecules with the following:

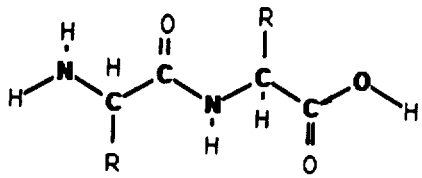
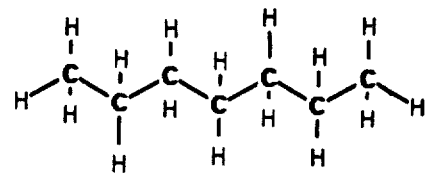
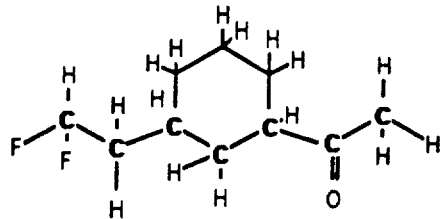
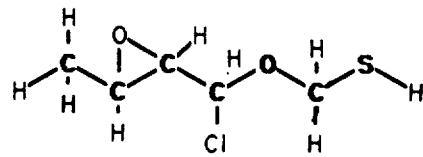

UNITED STATES PATENT AND TRADEMARK OFFICE
CERTIFICATE OF CORRECTION

PATENT NO. : 5,242,810  
DATED : September 7, 1993  
INVENTOR(S) : John M. Maraganore et al.

Page 2 of 2

It is certified that error appears in the above-identified patent and that said Letters Patent is hereby corrected as shown below:

```
Column 10, line 1, after "No:4" insert -- ) --.
Column 13, line 14, "Clu" should be -- Glu --.
Column 17, lines 27, 48 and 50 "hose" should be -- host --.
Column 18, line 63, "hose" should be -- host --.
Column 28, line 21, "appilog" should be -- Appilog --.
Column 29, line 3, before "amylose" delete -- a --.
Column 30, line 40, after "must" insert -- be --.
Column 31, line 10, "dosedependent" should be
                    -- dose-dependent --.
Column 32, lines 62-63, after "randomized" delete
                    -- the --.
```

Signed and Sealed this

Twenty-ninth Day of March, 1994

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 72 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Glu Ala Gly Glu Glu Cys Asp Cys Gly Ser Pro Glu Asn Pro Cys Asp
 1               5                  10                  15

Asp Ala Ala Thr Cys Lys Leu Arg Pro Gly Ala Gln Cys Ala Glu Gly
                20                  25                  30

Leu Cys Cys Asp Gln Cys Lys Phe Xaa Lys Glu Gly Thr Val Cys Arg
            35                  40                  45

Arg Ala Arg Gly Asp Asp Val Asn Asp Tyr Cys Asn Gly Ile Ser Ala
        50                  55                  60

Gly Cys Pro Arg Asn Pro Phe His
65                  70
```

( 2 ) INFORMATION FOR SEQ ID NO:2:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gly Pro Arg Pro Gly Gly Gly Gly Asn Gly Asp Phe Glu Glu Ile Pro
 1               5                  10                  15

Glu Glu Tyr Leu Gly Gly Gly Gly Glu Ala Gly Glu Glu Cys Asp Cys
                20                  25                  30

Gly Ser Pro Glu Asn Pro Cys Asp Asp Ala Ala Thr Cys Lys Leu Arg
            35                  40                  45

Pro Gly Ala Gln Cys Ala Glu Gly Leu Cys Cys Asp Gln Cys Lys Phe
        50                  55                  60

Xaa Lys Glu Gly Thr Val Cys Arg Arg Ala Arg Gly Asp Asp Val Asn
65                  70                  75                  80

Asp Tyr Cys Asn Gly Ile Ser Ala Gly Cys Pro Arg Asn Pro Phe His
                85                  90                  95
```

( 2 ) INFORMATION FOR SEQ ID NO:3:

( i ) SEQUENCE CHARACTERISTICS:
        ( A ) LENGTH: 96 amino acids
        ( B ) TYPE: amino acid -continued (D) TOPOLOGY: linear (ii) MOLECULE TYPE: protein (xi) SEQUENCE DESCRIPTION: SEQ ID NO:3:

```
Glu Ala Gly Glu Glu Cys Asp Cys Gly Ser Pro Glu Asn Pro Cys Asp
 1               5                  10                      15

Asp Ala Ala Thr Cys Lys Leu Arg Pro Gly Ala Gln Cys Ala Glu Gly
             20                  25                  30

Leu Cys Cys Asp Gln Cys Lys Phe Xaa Lys Glu Gly Thr Val Cys Arg
         35                  40                  45

Arg Ala Arg Gly Asp Asp Val Asn Asp Tyr Cys Asn Gly Ile Ser Ala
     50                  55                  60

Gly Cys Pro Arg Asn Pro Phe His Gly Gly Gly Gly Gly Pro Arg Pro
 65              70                  75                      80

Gly Gly Gly Gly Asn Gly Asp Phe Glu Glu Ile Pro Glu Glu Tyr Leu
                 85                  90                  95
```

(2) INFORMATION FOR SEQ ID NO:4:

(i) SEQUENCE CHARACTERISTICS:
(A) LENGTH: 106 amino acids
(B) TYPE: amino acid
(D) TOPOLOGY: linear (ii) MOLECULE TYPE: protein (xi) SEQUENCE DESCRIPTION: SEQ ID NO:4:

```
Gly Ser Ile Glu Gly Arg Pro Glu Phe Met Gly Pro Arg Pro Gly Gly
 1               5                  10                      15

Gly Gly Asn Gly Asp Phe Glu Glu Ile Pro Glu Glu Tyr Leu Gly Gly
             20                  25                  30

Gly Gly Glu Ala Gly Glu Glu Cys Asp Cys Gly Ser Pro Glu Asn Pro
         35                  40                  45

Cys Asp Asp Ala Ala Thr Cys Lys Leu Arg Pro Gly Ala Gln Cys Ala
     50                  55                  60

Glu Gly Leu Cys Cys Asp Gln Cys Lys Phe Met Lys Glu Gly Thr Val
 65              70                  75                      80

Cys Arg Arg Ala Arg Gly Asp Asp Val Asn Asp Tyr Cys Asn Gly Ile
                 85                  90                  95

Ser Ala Gly Cys Pro Arg Asn Pro Phe His
             100                 105
```

(2) INFORMATION FOR SEQ ID NO:5:

(i) SEQUENCE CHARACTERISTICS:
(A) LENGTH: 99 amino acids
(B) TYPE: amino acid
(D) TOPOLOGY: linear (ii) MOLECULE TYPE: protein (xi) SEQUENCE DESCRIPTION: SEQ ID NO:5:

```
Ala Asn Ser Gly Pro Arg Pro Gly Gly Gly Gly Asn Gly Asp Phe Glu
 1               5                  10                      15

Glu Ile Pro Glu Glu Tyr Leu Gly Gly Gly Gly Glu Ala Gly Glu Glu
             20                  25                  30

Cys Asp Cys Gly Ser Pro Glu Asn Pro Cys Asp Asp Ala Ala Thr Cys
         35                  40                  45

Lys Leu Arg Pro Gly Ala Gln Cys Ala Glu Gly Leu Cys Cys Asp Gln
     50                  55                  60

Cys Lys Phe Met Lys Glu Gly Thr Val Cys Arg Arg Ala Arg Gly Asp
```

|   | 65 |   |   | 70 |   |   |   | 75 |   |   |   | 80 |
|---|---|---|---|---|---|---|---|---|---|---|---|---|

Asp Val Asn Asp Tyr Cys Asn Gly Ile Ser Ala Gly Cys Pro Arg Asn
                    85                  90                  95

Pro Phe His (2) INFORMATION FOR SEQ ID NO:6:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Ile Met Gly Pro Arg Pro Gly Gly Gly Asn Gly Asp Phe Glu Glu
 1               5                   10                  15

Ile Pro Glu Glu Tyr Leu Gly Gly Gly Gly Glu Ala Gly Glu Glu Cys
                20                  25                  30

Asp Cys Gly Ser Pro Glu Asn Pro Cys Asp Asp Ala Ala Thr Cys Lys
            35                  40                  45

Leu Arg Pro Gly Ala Gln Cys Ala Glu Gly Leu Cys Cys Asp Gln Cys
 50                      55                  60

Lys Phe Leu Lys Glu Gly Thr Val Cys Arg Arg Ala Arg Gly Asp Asp
 65                  70                  75                  80

Val Asn Asp Tyr Cys Asn Gly Ile Ser Ala Gly Cys Pro Arg Asn Pro
                85                  90                  95

Phe His (2) INFORMATION FOR SEQ ID NO:7:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Gly Ser Ile Glu Gly Arg Pro Glu Phe Met Glu Ala Gly Glu Glu Cys
 1               5                   10                  15

Asp Cys Gly Ser Pro Glu Asn Pro Cys Asp Asp Ala Ala Thr Cys Lys
                20                  25                  30

Leu Arg Pro Gly Ala Gln Cys Ala Glu Gly Leu Cys Cys Asp Gln Cys
            35                  40                  45

Lys Phe Met Lys Glu Gly Thr Val Cys Arg Arg Ala Arg Gly Asp Asp
 50                  55                      60

Val Asn Asp Tyr Cys Asn Gly Ile Ser Ala Gly Cys Pro Arg Asn Pro
 65                  70                  75                  80

Phe His Gly Gly Gly Gly Gly Pro Arg Pro Gly Gly Gly Gly Asn Gly
                 85                 90                  95

Asp Phe Glu Glu Ile Pro Glu Glu Tyr Leu
             100                 105

(2) INFORMATION FOR SEQ ID NO:8:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Ala | Asn | Ser | Glu | Ala | Gly | Glu | Glu | Cys | Asp | Cys | Gly | Ser | Pro | Glu | Asn |
| 1 | | | | 5 | | | | | 10 | | | | | | 15 |

| Pro | Cys | Asp | Asp | Ala | Ala | Thr | Cys | Lys | Leu | Arg | Pro | Gly | Ala | Gln | Cys |
| | | | 20 | | | | | 25 | | | | | 30 | | |

| Ala | Glu | Gly | Leu | Cys | Cys | Asp | Gln | Cys | Lys | Phe | Met | Lys | Glu | Gly | Thr |
| | | 35 | | | | | 40 | | | | | 45 | | | |

| Val | Cys | Arg | Arg | Ala | Arg | Gly | Asp | Asp | Val | Asn | Asp | Tyr | Cys | Asn | Gly |
| | 50 | | | | | 55 | | | | | 60 | | | | |

| Ile | Ser | Ala | Gly | Cys | Pro | Arg | Asn | Pro | Phe | His | Gly | Gly | Gly | Gly | Gly |
| 65 | | | | | 70 | | | | | 75 | | | | | 80 |

| Pro | Arg | Pro | Gly | Gly | Gly | Gly | Asn | Gly | Asp | Phe | Glu | Glu | Ile | Pro | Glu |
| | | | | 85 | | | | | 90 | | | | | 95 | |

| Glu | Tyr | Leu |

( 2 ) INFORMATION FOR SEQ ID NO:9:

( i ) SEQUENCE CHARACTERISTICS:
( A ) LENGTH: 98 amino acids
( B ) TYPE: amino acid
( D ) TOPOLOGY: linear ( i i ) MOLECULE TYPE: protein ( x i ) SEQUENCE DESCRIPTION: SEQ ID NO:9:

| Ile | Met | Glu | Ala | Gly | Glu | Glu | Cys | Asp | Cys | Gly | Ser | Pro | Glu | Asn | Pro |
| 1 | | | | 5 | | | | | 10 | | | | | 15 | |

| Cys | Asp | Asp | Ala | Ala | Thr | Cys | Lys | Leu | Arg | Pro | Gly | Ala | Gln | Cys | Ala |
| | | | 20 | | | | | 25 | | | | | 30 | | |

| Glu | Gly | Leu | Cys | Cys | Asp | Gln | Cys | Lys | Phe | Leu | Lys | Glu | Gly | Thr | Val |
| | | 35 | | | | | 40 | | | | | 45 | | | |

| Cys | Arg | Arg | Ala | Arg | Gly | Asp | Asp | Val | Asn | Asp | Tyr | Cys | Asn | Gly | Ile |
| | 50 | | | | | 55 | | | | | 60 | | | | |

| Ser | Ala | Gly | Cys | Pro | Arg | Asn | Pro | Phe | His | Gly | Gly | Gly | Gly | Gly | Pro |
| 65 | | | | | 70 | | | | | 75 | | | | | | 80 |

| Arg | Pro | Gly | Gly | Gly | Gly | Asn | Gly | Asp | Phe | Glu | Glu | Ile | Pro | Glu | Glu |
| | | | | 85 | | | | | 90 | | | | | 95 | |

| Tyr | Leu |

( 2 ) INFORMATION FOR SEQ ID NO:10:

( i ) SEQUENCE CHARACTERISTICS:
( A ) LENGTH: 288 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: N ( i v ) ANTI-SENSE: N ( x i ) SEQUENCE DESCRIPTION: SEQ ID NO:10:

| GGTCCGCGTC | CGGGTGGTGG | TGGTAACGGT | GACTTCGAAG | AAATCCCGGA | AGAATACCTG | 60 |
| GGTGGTGGTG | GTGAAGCTGG | TGAAGAATGC | GACTGCGGAT | CCCCGGAAAA | CCCGTGCGAC | 120 |
| GACGCTGCTA | CCTGCAAACT | GCGTCCGGGT | GCTCAGTGCG | CTGAAGGTCT | GTGCTGCGAC | 180 |
| CAGTGCAAAT | TCNNNAAAGA | AGGTACCGTT | TGCCGTCGTG | CTCGTGGTGA | CGACGTTAAC | 240 |
| GACTACTGCA | ACGGTATCTC | TGCAGGTTGC | CCGCGTAACC | CGTTCCAC | | 288 |

( 2 ) INFORMATION FOR SEQ ID NO:11:

( i ) SEQUENCE CHARACTERISTICS:
        ( A ) LENGTH: 288 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( x i ) SEQUENCE DESCRIPTION: SEQ ID NO:11:

```
GAAGCTGGTG AAGAATGCGA CTGCGGATCC CCGGAAAACC CGTGCGACGA CGCTGCTACC    60
TGCAAACTGC GTCCGGGTGC TCAGTGCGCT GAAGGTCTGT GCTGCGACCA GTGCAAATTC   120
NNNAAAGAAG GTACCGTTTG CCGTCGTGCT CGTGGTGACG ACGTTAACGA CTACTGCAAC   180
GGTATCTCTG CAGGTTGCCC GCGTAACCCG TTCCACGGTG GTGGTGGTGG TCCGCGTCCG   240
GGTGGTGGTG GTAACGGTGA CTTCGAAGAA ATCCGGAAG AATACCTG                 288
```

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( x i ) SEQUENCE DESCRIPTION: SEQ ID NO:12:

```
AATTCGGAAG CTGGTGAAGA ATGCGACTGC G                                   31
```

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( x i ) SEQUENCE DESCRIPTION: SEQ ID NO:13:

```
GATCCGCAGT CGCATTCTTC ACCAGCTTCC G                                   31
```

( 2 ) INFORMATION FOR SEQ ID NO:14:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( x i ) SEQUENCE DESCRIPTION: SEQ ID NO:14:

```
AATTCGGGTC CGCGTCCGGG TGGTGGTGGT AACGGTGACT T                        41
```

(2) INFORMATION FOR SEQ ID NO:15:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: cDNA (iii) HYPOTHETICAL: N (iv) ANTI-SENSE: N (xi) SEQUENCE DESCRIPTION: SEQ ID NO:15:

CGAAGTCACC GTTACCACCA CCACCCGGAC GCGGACCCG                            39

(2) INFORMATION FOR SEQ ID NO:16:

(i) SEQUENCE CHARACTERISTICS:
      (A) LENGTH: 51 base pairs
      (B) TYPE: nucleic acid
      (C) STRANDEDNESS: single
      (D) TOPOLOGY: linear (ii) MOLECULE TYPE: cDNA (iii) HYPOTHETICAL: N (iv) ANTI-SENSE: N (xi) SEQUENCE DESCRIPTION: SEQ ID NO:16:

ACGTCGGTAC CAGGCGCGCG TATCGAGGGT AGGATCATGG AAGCTGGTGA A              51

(2) INFORMATION FOR SEQ ID NO:17:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (iii) HYPOTHETICAL: N (iv) ANTI-SENSE: N (xi) SEQUENCE DESCRIPTION: SEQ ID NO:17:

GCAAACGGTA CCTTCTTTCA GGAATTTGCA CTGGTC                               36

(2) INFORMATION FOR SEQ ID NO:18:

(i) SEQUENCE CHARACTERISTICS:
      (A) LENGTH: 20 amino acids
      (B) TYPE: amino acid
      (D) TOPOLOGY: linear (ii) MOLECULE TYPE: protein (xi) SEQUENCE DESCRIPTION: SEQ ID NO:18:

Phe Pro Arg Pro Gly Gly Gly Gly Asn Gly Asp Phe Glu Glu Ile Pro
 1               5                   10                  15

Glu Glu Tyr Leu
        20